United States Patent
Kleinschmidt et al.

(10) Patent No.: US 11,045,533 B2
(45) Date of Patent: Jun. 29, 2021

(54) HUMANIZED ANTIBODIES

(71) Applicant: Probiodrug AG, Halle (DE)

(72) Inventors: Martin Kleinschmidt, Halle (DE); Jens-Ulrich Rahfeld, Gemeinde Seegebiet Mansfelder Land (DE); Anke Piechotta, Halle (DE); Stephan Schilling, Halle (DE); Stephen Gillies, Carlisle, MA (US)

(73) Assignee: PROBIODRUG AG

( * ) Notice: Subject to any disclaimer, the term of this patent is extended or adjusted under 35 U.S.C. 154(b) by 0 days.

(21) Appl. No.: 16/744,404

(22) Filed: Jan. 16, 2020

(65) Prior Publication Data

US 2020/0138922 A1 May 7, 2020

Related U.S. Application Data

(60) Division of application No. 15/866,773, filed on Jan. 10, 2018, now Pat. No. 10,603,367, which is a continuation-in-part of application No. PCT/EP2016/066924, filed on Jul. 15, 2016.

(60) Provisional application No. 62/209,650, filed on Aug. 25, 2015, provisional application No. 62/193,356, filed on Jul. 16, 2015.

(51) Int. Cl.
| | |
|---|---|
| *A61K 39/00* | (2006.01) |
| *C07K 16/18* | (2006.01) |
| *A61P 25/14* | (2006.01) |
| *A61P 25/28* | (2006.01) |
| *A61K 39/395* | (2006.01) |
| *G01N 33/68* | (2006.01) |

(52) U.S. Cl.
CPC ...... *A61K 39/0008* (2013.01); *A61K 39/3955* (2013.01); *A61P 25/14* (2018.01); *A61P 25/28* (2018.01); *C07K 16/18* (2013.01); *G01N 33/6896* (2013.01); *A61K 2039/505* (2013.01); *C07K 2317/24* (2013.01); *C07K 2317/565* (2013.01); *C07K 2317/567* (2013.01); *C07K 2317/75* (2013.01); *C07K 2317/76* (2013.01); *C07K 2317/92* (2013.01); *G01N 2333/4709* (2013.01); *G01N 2800/2821* (2013.01)

(58) Field of Classification Search
CPC ............ A61K 39/0008; A61K 39/3955; A61K 2039/505; G01N 33/6896; G01N 2333/4709; G01N 2800/2821; C07K 16/18; C07K 2317/92; C07K 2317/565; C07K 2317/567; C07K 2317/75; C07K 2317/76; C07K 2317/24; A61P 25/14; A61P 25/28

See application file for complete search history.

*Primary Examiner* — Kimberly Ballard
*Assistant Examiner* — Stacey N MacFarlane
(74) *Attorney, Agent, or Firm* — Olson & Cepuritis, Ltd.

(57) ABSTRACT

The invention relates to humanized antibodies that bind to an epitope at the N-terminus of pyroglutamated amyloid beta (Aβ N3pE) peptide and to preventive and therapeutic treatment of diseases and conditions that are related to accumulation and deposition of amyloid peptides, such as amyloidosis, a group of disorders and abnormalities associated with pyroglutamated amyloid peptide, like Alzheimer's disease, Down's syndrome, cerebral amyloid angiopathy and other related aspects. More specifically, it pertains to the use of humanized monoclonal antibodies to bind pyroglutamated amyloid beta peptide in plasma, brain, and cerebrospinal fluid to prevent accumulation or to reverse deposition of Aγ N3pE within the brain and in various tissues in the periphery, and to alleviate amyloidosis. The present invention further pertains to diagnostic assays for the diagnosis of amyloidosis using the humanized antibodies of the invention.

18 Claims, 8 Drawing Sheets

Specification includes a Sequence Listing.

Figure 1

```
LC:                         CDR1                                    CDR2
DVVMTQTPLTLSVTIGQPASISC KSSQSLLYSDGKTYLH WLLQRPGQSPMRLIY LVSKLDS GVPDRFTG
SGSGTDFTLKISRVEAEDLGVYYC VQGTHFPFT FGSGTKLEIKR
                          CDR3
HC:                         CDR1                                    CDR2
EVQLQQSGPELVKPGASMKISCKAS GYSFTGYTMN WVKQSHGKNLEWIG LINPYNGVTRYNQKFKG
KATLIVDKSSSTAYMELLSLTSEDSAVYYCTR EAKKEWDFTY WGQ
                                    CDR3
```

HUMANIZED ANTIBODIES

CROSS-REFERENCE TO RELATED APPLICATIONS

This application is a division of U.S. patent application Ser. No. 15/866,773, filed on Jan. 10, 2018, which is a continuation-in-part of PCT/EP2016/066924, filed on Jul. 15, 2016, and claims the benefit of U.S. Provisional Application No. 62/209,650, filed on Aug. 25, 2015, and U.S. Provisional Application No. 62/193,356, filed on Jul. 16, 2015, each of which is incorporated herein by reference.

FIELD OF THE INVENTION

The invention relates to humanized antibodies that bind to an epitope at the N-terminus of pyroglutamated amyloid beta (Aβ N3pE) peptide and to preventive and therapeutic treatment of diseases and conditions that are related to accumulation and deposition of amyloid peptides, such as amyloidosis, a group of disorders and abnormalities associated with pyroglutamated amyloid peptide, like Alzheimer's disease, Down's syndrome, cerebral amyloid angiopathy and other related aspects. More specifically, it pertains to the use of humanized monoclonal antibodies to bind pyroglutamated amyloid beta peptide in plasma, brain, and cerebrospinal fluid to prevent accumulation or to reverse deposition of Aβ N3pE within the brain and in various tissues in the periphery, and to alleviate amyloidosis. The present invention further pertains to diagnostic assays for the diagnosis of amyloidosis using the humanized antibodies of the invention.

SEQUENCE LISTING INCORPORATION

Biological sequence information for this application is included in an ASCII text file, having the file name "MAI-211-DIV_SEQ.txt", created on Jan. 15, 2020, and having a file size of 40,710 bytes, which is incorporated herein by reference.

BACKGROUND ART

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease and leprosy.

Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome, Lewy body dementia, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., Tohoku J Exp Med. 174(3): 269-277 (1994)).

Recently, accumulating evidence demonstrates involvement of N-terminal modified Aβ peptide variants in Alzheimer's disease. Aiming biopsies display a presence of Aβ 1-40 and Aβ 1-42 not only in the brain of Alzheimer's patients but also in senile plaques of unaffected individuals. However, N-terminal truncated and pyroGlu modified Aβ N3pE-40/Aβ N3pE-42 is almost exclusively engrained within plaques of Alzheimer's disease patients, making this Aβ variant an eligible diagnostic marker and a potential target for drug development.

At present, several commercial manufacturers offer ELISA kits which allow a detection of Aβ 1-40/1-42 and Aβ N3pE-40/Aβ N3pE-42 in the low picogram (pg) range.

The brains of Alzheimer's disease (AD) patients are morphologically characterized by the presence of neurofibrillary tangles and by deposits of Aβ peptides in neocortical brain structures (Selkoe, D. J. & Schenk, D. Alzheimer's disease: molecular understanding predicts amyloid-based therapeutics. Annu. Rev. Pharmacol. Toxicol. 43, 545-584 (2003)). Aβ peptides are liberated from the amyloid precursor protein (APP) after sequential cleavage by β- and γ-secretase. The γ-secretase cleavage results in the generation of Aβ 1-40 and Aβ 1-42 peptides, which differ in their C-termini and exhibit different potencies of aggregation, fibril formation and neurotoxicity (Shin, R. W. et al. Amyloid beta-protein (Abeta) 1-40 but not Abeta 1-42 contributes to the experimental formation of Alzheimer disease amyloid fibrils in rat brain. J. Neurosci. 17, 8187-8193 (1997); Iwatsubo, T. et al. Visualization of Abeta 42(43) and Abeta 40 in senile plaques with end-specific Abeta monoclonals: evidence that an initially deposited species is Abeta 42(43). Neuron 13, 45-53 (1994); Iwatsubo, T., Mann, D. M., Odaka, A., Suzuki, N. & Ihara, Y. Amyloid beta protein (Abeta) deposition: Abeta 42(43) precedes Abeta 40 in Down syndrome. Ann. Neurol. 37, 294-299 (1995); Hardy, J. A. & Higgins, G. A. Alzheimer's disease: the amyloid cascade hypothesis. Science 256, 184-185 (1992); Rolner, S., Ueberham, U., Schliebs, R., Perez-Polo, J. R. & Bigl, V.

The regulation of amyloid precursor protein metabolism by cholinergic mechanisms and neurotrophin receptor signaling. Prog. Neurobiol. 56, 541-569 (1998)).

The majority of Aβ peptides deposited in diffuse plaques are N-terminal truncated or modified. Studies of Piccini and Saido have shown that the core structure of senile plaques and vascular deposits consist of 50% pyroglutamate (pyroGlu) modified peptides (Piccini et al., J Biol Chem. 2005 Oct. 7; 280(40):34186-92; Saido et al., Neuron. 1995 February; 14(2): 457-66). PyroGlu modified peptides are more strongly cytotoxic than other Aβ species and stable against aminopeptidases (Russo et al., J Neurochem. 2002 September; 82(6):1480-9). Thus, pyroGlu Aβ species have a longer half-life whereby the accumulation of these species and the formation of neurotoxic oligomers as well as aggregates are beneficial (Saido, Neurobiol Aging. 1998 January-February; 19(1 Suppl):S69-75). Due to the cyclization of glutamate to pyroGlu, charged amino acids will be lost which strongly reduces the solubility of the peptide and causes an increased aggregation tendency. In vitro studies have shown that the initial oligomerisation of e.g. Aβ3(pE) is much faster compared to non-modified peptides (Schilling et al., Biochemistry. 2006 Oct. 17; 45(41):12393-9). The Aβ N3pE-42 peptides coexist with Aβ 1-40/1-42 peptides (Saido, T. C. et al. Dominant and differential deposition of distinct beta-amyloid peptide species, Abeta N3pE, in senile plaques. Neuron 14, 457-466 (1995); Saido, T. C., Yamao, H., Iwatsubo, T. & Kawashima, S. Amino- and carboxyl-terminal heterogeneity of beta-amyloid peptides deposited in human brain. Neurosci. Lett. 215, 173-176 (1996)), and, based on a number of observations, could play a prominent role in the pathogenesis of AD. For example, a particular neurotoxicity of Aβ N3pE-42 peptides has been outlined (Russo, C. et al. Pyroglutamate-modified amyloid beta-peptides—AbetaN3(pE)—strongly affect cultured neuron and astrocyte survival. J. Neurochem. 82, 1480-1489 (2002) and the pE-modification of N-truncated Aβ peptides confers resistance to degradation by most aminopeptidases as well as Aβ-degrading endopeptidases (Russo, C. et al. Pyroglutamate-modified amyloid beta-peptides—AbetaN3(pE)— strongly affect cultured neuron and astrocyte survival. J. Neurochem. 82, 1480-1489 (2002); Saido, T. C. Alzheimer's disease as proteolytic disorders: anabolism and catabolism of beta-amyloid. Neurobiol. Aging 19, S69-S75 (1998)). The cyclization of glutamic acid into pE leads to a loss of N-terminal charge resulting in accelerated aggregation of Aβ N3pE compared to the unmodified Aβ peptides (He, W. & Barrow, C. J. The Abeta 3-pyroglutamyl and 11-pyroglutamyl peptides found in senile plaque have greater beta-sheet forming and aggregation propensities in vitro than full-length A beta. Biochemistry 38, 10871-10877 (1999); Schilling, S. et al. On the seeding and oligomerization of pGlu-amyloid peptides (in vitro). Biochemistry 45, 12393-12399 (2006)). Thus, reduction of Aβ N3pE-42 formation should destabilize the peptides by making them more accessible to degradation and would, in turn, prevent the formation of higher molecular weight Aβ aggregates and enhance neuronal survival.

However, for a long time it was not known how the pE-modification of Aβ peptides occurs. Recently, it was discovered that glutaminyl cyclase (QC) is capable to catalyze Aβ N3pE-42 formation under mildly acidic conditions and that specific QC inhibitors prevent Aβ N3pE-42 generation in vitro (Schilling, S., Hoffmann, T., Manhart, S., Hoffmann, M. & Demuth, H.-U. Glutaminyl cyclases unfold glutamyl cyclase activity under mild acid conditions. FEBS Lett. 563, 191-196 (2004); Cynis, H. et al. Inhibition of glutaminyl cyclase alters pyroglutamate formation in mammalian cells. Biochim. Biophys. Acta 1764, 1618-1625 (2006)).

All facts suggest that pyroGlu Aβ is a kind of germ for the initialization of fibril formation. In a further study (Piccini et al., 2005, supra) volunteers with plaque depositions but without AD specific pathology could be distinguished from AD patients due to the characteristic amount of Aβ-species. Thereby the amount of N-terminal truncated, pyroGlu modified peptides was significant higher in the brain of AD patients.

The posttranslational formation of pyroGlu at position 3 or 11 of Aβ-peptide implies cyclization of an N-terminal glutamate residue. Glutaminyl cyclase (QC) plays an important role in the generation of pyroGlu peptides. QC is wide-spread in the plant- and animal kingdom and inter alia, is involved in the maturation of peptide hormones. Both the cyclisation of glutamine by release of ammonia and of glutamate by release of water to pyroGlu is performed by QC. In contrast to the glutamine cyclization the glutamate cyclisation occurs not spontaneously. QC catalyses the efficient (unwanted) side reaction from glutamate to pyroGlu. The generated pyroGlu residue protects the protein against proteolytic degradation. There are several references which shows that QC plays an important role in the generation of pyroGlu Aβ:

1. In several studies it was shown that QC catalyses the formation of pyroGlu residues from glutamate at N-terminus of Aβ (Cynis et al., Biochim Biophys Acta. 2006 October; 1764(10):1618-25, Schilling et al., FEBS Lett. 2004 Apr. 9; 563(1-3):191-6);
2. Both Aβ peptides and QC are expressed in large quantities in hippocampus and cortex. These brain areas are at particular risk in AD (Pohl et al., Proc Natl Acad Sci USA. 1991 Nov. 15; 88(22):10059-63, Selkoe, Physiol Rev. 2001 April; 81(2):741-66);
3. The APP is cleaved by β-secretase during the transport to the plasma membrane whereby the N-terminus of Aβ with the free glutamate residue can be produced (Greenfield et al., Proc Natl Acad Sci USA. 1999 Jan. 19; 96(2):742-7). In the secretory vesicles a co-localisation of processed APP and the QC was determined. So in the mild acid milieu of the vesicles an accelerated modification of glutamate residue to pyroglutamate can occur.
4. Also other neurodegenerative diseases (familiar Danish (FDD) or British dementia (FBD)) are related with N-terminal pyroGlu modified peptides e.g. Bri2, but in contrast they are not related to Aβ in terms of their primary structure (Vidal R. et al., 1999 Proc. Natl. Acad. Sci. U.S.A. 97, 4920-4925).

Possibly the QC-catalysed formation of pyroGlu Aβ is involved in the development and progression of neurodegenerative diseases. The formation of N-terminal modified amyloid peptides certainly represents a fundamental factor in the process of Aβ aggregation and could be the onset of disease. The suppression of the pyroGlu Aβ formation by inhibition of QC, might represent a therapeutic approach. QC inhibitors would be able to prevent the formation of pyroGlu Aβ, reduce the concentration of pyroglutamate Aβ in the brain and so delay the oligomerisation of Aβ-peptides. Schilling et al. show, that QC expression was up regulated in the cortex of AD patients and correlated with the appearance of pyroGlu-modified Aβ-peptide. Oral application of a QC inhibitor resulted in reduced pyroglutamate modified AβpE(3-42) level in two different transgenic mouse models of AD and in a new *Drosophila* model (Schilling et al., 2008 *Biol. Chem.* (389), 983-991).

Lewy body dementia (LBD) is a neurodegenerative disorder that can occur in persons older than 65 years of age, and typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days. Lewy bodies are formed from phosphorylated and nonphosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of LBD but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration. Macular degeneration is a common eye disease that causes deterioration of the macula, which is the central area of the retina (the paper-thin tissue at the back of the eye where light-sensitive cells send visual signals to the brain). Sharp, clear, "straight ahead" vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans of age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contain amyloid beta. (Experimental Eye Research 78 (2004) 243-256).

Pyroglutamated Aβ peptides have been shown to play a key role in accumulation of Aβ peptides and in plaque formation in Alzheimer's diseases. Due to their hydrophobic potential it has been shown that these peptides promote aggregation and plaque formation. It has further been shown in a transgenic mouse model expressing Aβ N3pE-42 in neurons that this peptide is neurotoxic in vivo and leads to loss of neurons (Wirths et al. (2009) Acta Neuropatho/118, 487-496).

Antibodies with specificities against the N-terminal pyroglutamate of Aβ peptides are believed to be advantageous because of their specificity towards only the pathogenic species of Aβ, which carry a pyroglutamate at the N-terminus, but not detecting APP or other Aβ species w/o the N-terminal pyroglutamate. It is thus believed that the risk of potential side effects, such as uncontrollable cerebral inflammation, will be reduced by use of the antibodies of the invention compared to antibodies directed to other Aβ species that the pyroglutamated variants.

Antibodies targeting Aβ N3pE peptides are known (Acero et al (2009) J Neuroimmunol 213, 39-46; Saido et al. (1996) Neuron 14, 457-466; U.S. Pat. No. 7,122,374 and WO 2012/136552).

However, there is a need for humanized antibodies with specificity for Aβ N3pE peptides that can be used in human treatment and that positively affect amyloidosis, in particular cognition in diseases and conditions where Aβ N3pE may be involved, such as clinical or pre-clinical Alzheimer's disease, Down's syndrome, and clinical or pre-clinical cerebral amyloid angiopathy.

SUMMARY OF THE INVENTION

The invention provides novel methods and compositions comprising highly specific and highly effective antibodies, including chimeric antibodies and fragments thereof, including partially or fully humanized antibodies and fragments thereof, having the ability to specifically recognize and bind to specific epitopes from a range of β-amyloid antigens, in particular Aβ N3pE peptides, which may be presented to the antibody in a monomeric, dimeric, trimeric, etc, or a polymeric form, in form of an aggregate, fibers, filaments or in the condensed form of a plaque.

In particular, the present invention pertains to a humanized antibody or a functional variant thereof, wherein the variable part of the light chain of said antibody comprises, consists essentially of or consists of an amino acid sequence of:

(SEQ ID NO: 7)
DVVMTQSPLSLPVTLGQPASISCKSSQSLLX$_1$SDGKTYLNWFQQRPGQSP

RRLX$_2$YLVSKLDSGVPDRFSGSGSGTDFTLKISRVEAEDVGVYYCVQGTH

FPFTFGGGTKVEIK, wherein
X$_1$ is selected from Y and H; and
X$_2$ is selected from A, I and T;
or of an amino acid sequence selected from (SEQ ID NO: 28)
DIQMTQSPSSLSASVGDRVTITCRSSQSLVHSDGNTYLHWYQQKPGKAPK

LLIYKVSNRFSGVPSRFSGSGSGTDFTLTISSLQPEDFATYYCSQSTHVP

PTFGQGTKVEIK;
and (SEQ ID NO: 36)
DVVMTQSPLSLPVTLGQPASISCKSSQSLLYSNGKTYLNWFQQRPGQSPR

RLIYVVSKLDSGVPDRFSGSGSGTDFTLKISRVEAEDVGVYYCVQGTHFP

FTFGGGTKVEIK.

and/or
wherein the variable part of heavy chain of said antibody comprises, consists essentially of or consists of an amino acid sequence of:

(SEQ ID NO: 17)
QVQLVQSGAEVKKSGASVKVSCKASGYSFTGX$_3$TMNWVRQAPGQGLEWMG

LINPX$_4$NX$_5$VTRYNQKFX$_6$GRVTX$_7$X$_8$RDTSTTTVX$_9$MELTSLTSEDTA

X$_{10}$YYCTREAKREWDETYWGQGTLVTVSS;

wherein
X$_3$ is selected from Y and H;
X$_4$ is selected from Y and S;
X$_5$ is selected from G, T, A and E;
X$_6$ is selected from K and Q;
X$_7$ is selected from L and I;
X$_8$ is selected from I and T;
X$_9$ is selected from Y and H; and
X$_{10}$ is selected from V and T;
or of an amino acid sequence selected from (SEQ ID NO: 32)
EVQLVESGGGLVQPGGSLRLSCAASGFTFSDYGMAWVRQAPGKGLEMSFI

SNLAYSIYYADTVTGRFTISRDNAKNSLYLQMNSLRAEDTAVYYCARYDY

DNILDYVMDYWGQGTLVTVSS,
and (SEQ ID NO: 40)
QVQLVESGAEVKKPGASVKVSCKASGYIFNNYWINWVRQAPGQGLEWMGQ

IYPGDGDTNYNGKFKGRVTITADESTSTAYMELSSLRSEDTAVYYCAREG

YIVYWGQGTLVTVSS.

The invention provides humanized antibodies, or fragments thereof, that positively affect diseases and conditions of amyloidosis, where Aβ N3pE may be involved.

In another embodiment, the invention provides humanized antibodies and fragments thereof that bind to Aβ N3pE peptides in the circulation and tissue, in particular in the brain. The humanized antibodies of the invention are capable of binding free Aβ N3pE peptide molecules or even bound forms of Aβ N3pE peptides.

Thus, the present invention further provides humanized antibodies that alter clearance of soluble and bound forms of Aβ N3pE peptides in the central nervous system, such as the brain, and the circulation, such as plasma.

In a further embodiment, the invention provides humanized antibodies and fragments thereof, wherein the humanized antibodies specifically bind to the pyroglutamate carrying N-terminus of Aβ N3pE.

In yet a further embodiment, the present invention also relates to the host cells transformed with the vectors or incorporating the polynucleotides that express the humanized antibodies or fragments thereof.

Moreover, the present invention provides pharmaceutical compositions comprising the humanized antibodies of the invention and fragments thereof.

The invention further relates to the use of the humanized antibodies and fragments thereof are useful for binding to and clearing or removing of Aβ N3pE in humans and thereby for diagnosing, preventing and treating diseases and conditions characterized by amyloidosis or Aβ N3pE toxicity.

In a particular embodiment, the humanized antibodies of the invention, which are capable of binding to and clearing or removing of Aβ N3pE peptides in biological fluids and tissues, are useful for the prevention and/or treatment of conditions associated with the formation of Aβ N3pE-containing plaques, such as diffuse, neuritic, and cerebrovascular plaques in the brain.

The administration of the humanized antibodies of the invention, including immunologically reactive fragments thereof, may lead to the clearance or removal of Aβ N3pE from the aforementioned plaques or other biological complexes. Thus, the humanized antibody of the invention will readily be transport in the circulation, other body fluids and to sites where the aforementioned plaques and/or other biological complexes are formed or elsewhere where AαN3pE exhibits damaging effects.

In addition, removal of Aβ N3pE from plaques or other biological complexes by the humanized antibodies of the invention may lead to the solubilization of insoluble forms of plaques and thus lead to the removal of complete plaques from the affected tissue, such as brain tissue. This, in turn, may lead to improvement of cognition in patients diagnosed with a neurodegenerative disease, such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD) or others, neurodegeneration in Down Syndrome, Lewy body dementia, hereditary cerebral hemorrhage with amyloidosis (Dutch type); the Guam Parkinson-Dementia complex.

The binding of the humanized antibodies of the invention to Aβ N3pE in the circulation or other body fluids may further result to the removal of the circulating or soluble forms of Aβ N3pE. As discussed above, Aβ N3pE exhibits a high hydrophobicity and has a high affinity to other, e.g. nonpyroglutamated Aβ peptides, which results in the formation of oligomeric and supermolecular structures, such as amyloid plaques. It has been shown that in particular these oligomeric structures are highly neurotoxic. The formation of oligomeric structures leads to cell damage and death of neuronal cells. Thus, the removal of circulating or soluble forms of Aβ N3pE or even of oligomers comprising Aβ N3pE leads to the prevention of cell damage and/or neurotoxicity. Thus, the invention also provides methods of preventing of neurodegenerative disease, such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD) or others, neurodegeneration in Down Syndrome, Lewy body dementia, hereditary cerebral hemorrhage with amyloidosis (Dutch type), the Guam Parkinson-Dementia complex.

The invention further provides methods of preventing and/or treating of other diseases which are based on or associated with amyloid-like proteins, in particular Aβ N3pE, such as progressive supranuclear palsy, multiple sclerosis, Creutzfeld Jacob disease, Parkinson's disease, HIV-related dementia, ALS (amyotropic lateral sclerosis), dementia related to Adult Onset Diabetes; senile cardiac amyloidosis, and others, including macular degeneration.

The invention further provides a highly sensitive and concomitantly robust detection technique that allows quantitative determination of Aβ variants, in particular Aβ N3pE, in biological samples, e.g. liquor or serum samples, preferably serum samples, or tissue samples. This is a tremendous challenge, taking the low abundance of these Aβ N3pE peptides in blood into account. Having such a detection technique available is, however, a prerequisite for studying efficacy of small molecule inhibitors in drug screening and drug development programs.

The antibodies enabled by the teaching of the present invention are particularly useful for diagnosis of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type), the Guam Parkinson-Dementia complex, as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), dementia related to Adult Onset Diabetes, senile cardiac amyloidosis, and others, including macular degeneration, to name just a few.

DESCRIPTION OF THE FIGURES

FIG. 1 shows the CDR definition of mouse antibody clone #6 Amino acid sequence of variable domain of light chain (LC) and heavy chain (HC) are shown. The three CDRs of LC and HC are framed (selected by Sircar et al., 2009 (Sircar A. et al.: RosettaAntibody: antibody variable region homology modeling server. Nucleic Acids Research, 2009, Vol. 37, pp. W474-W479) according to Kabat and Wu, 1971 (Kabat E. A. and WU, T. T.: An Attempt to Locate the Non-helical and Permissively Helical Sequences of Proteins: Application to the Variable Regions of Immunoglobulin Light and Heavy Chains. Proc. Nat. Acad. Sci. USA; Vol. 68, No. 7, pp. 1501-1506, 1971) and Kabat et al. 1991 (Kabat E. A. and WU, T. T.: IDENTICAL V REGION AMINO ACID SEQUENCES AND SEGMENTS OF SEQUENCES IN ANTIBODIES OF DIFFERENT SPECIFICITIES: Relative Contributions of VH and VL Genes, Minigenes, and Complementarity-Determining Regions to Binding of Antibody-Combining Sites. The Journal of Immunology, Vol. 147; pp. 1709-1719, 1991); beside CDR1 of HC which is defined according to Clothia et al., 1989 (Clothia C. et al.: Conformations of immunoglobulin hypervariable regions. Nature, Vol. 342, pp. 877-883, 1989).

Integration of raw data to represent the concentration of added peptide as a function molar ratio peptide/antibody. The values of the thermodynamic parameters are shown left.

Figure 6:
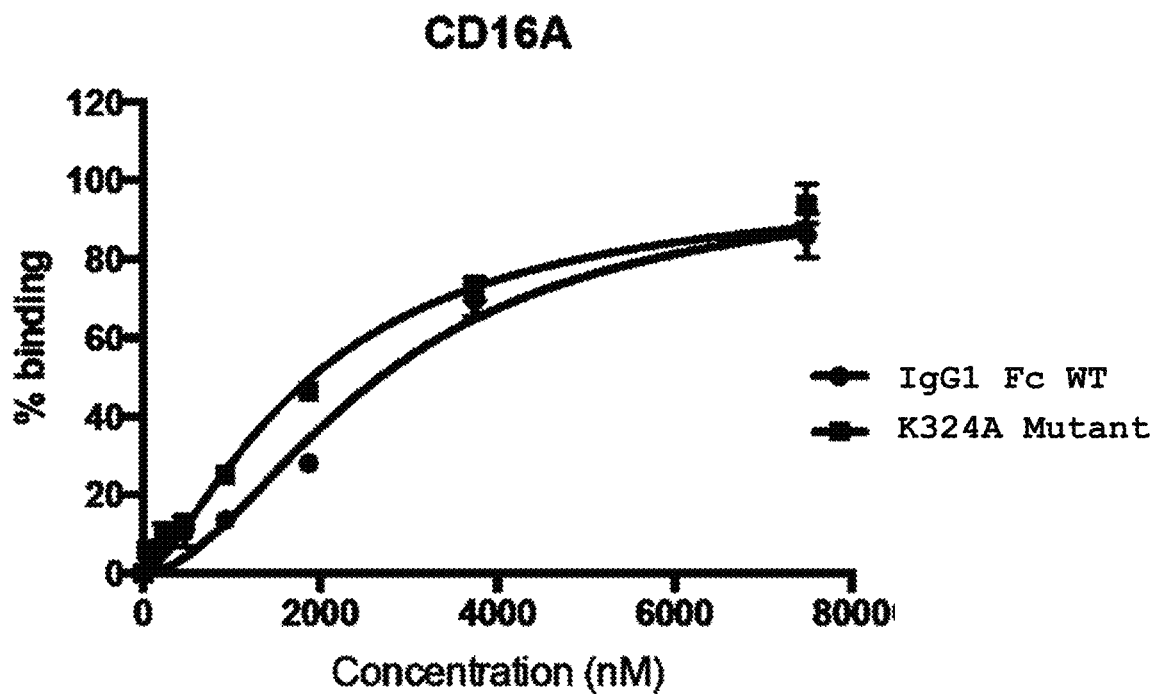

FIG. 6 shows the binding of two antibodies, which either comprise the human IgG1 Fc wild-type region of SEQ ID NO: 73 (WT) or the K324A mutant variant thereof (SEQ ID NO: 74), to the Fc gamma receptor CD16A.

Figure 7:
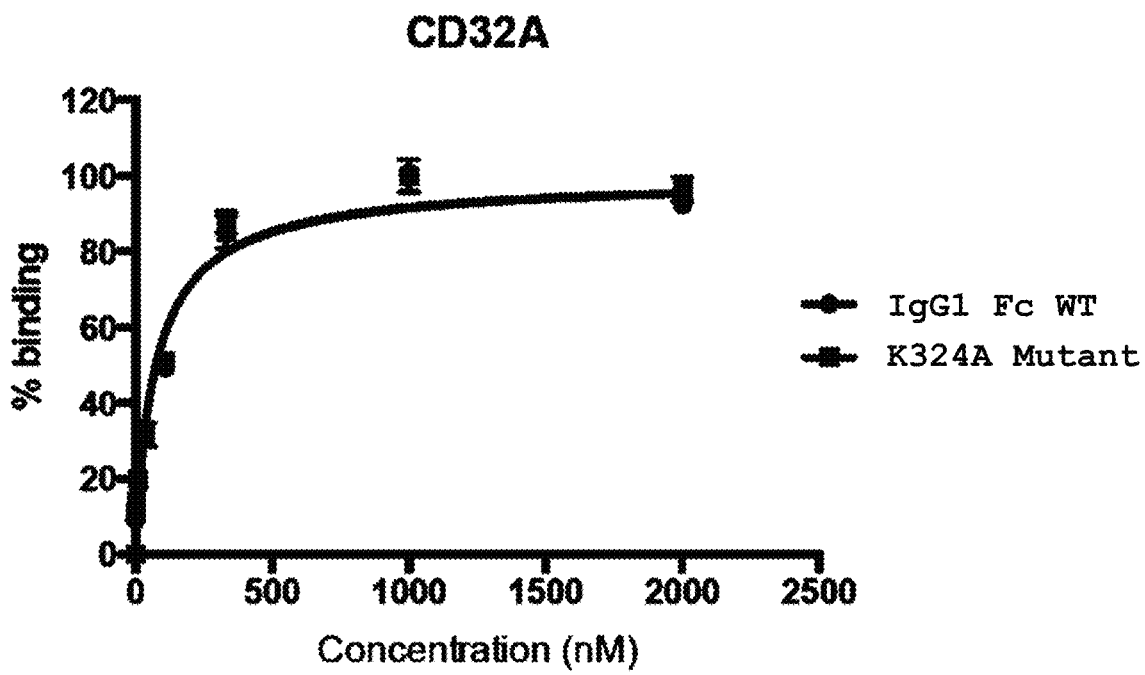

FIG. 7 shows the binding of two antibodies, which either comprise the human IgG1 Fc wild-type region of SEQ ID NO: 73 (WT) or the K324A mutant variant thereof (SEQ ID NO: 74), to the Fc gamma receptor CD32A.

Figure 8:
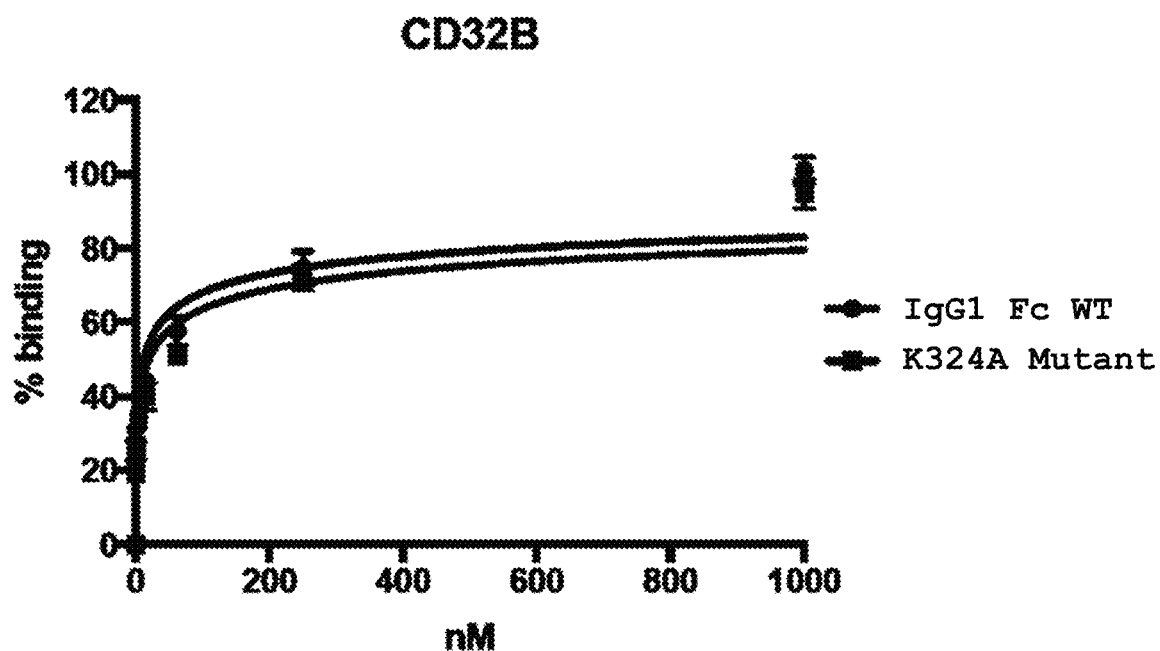

FIG. 8 shows the binding of two antibodies, which either comprise the human IgG1 Fc wild-type region of SEQ ID NO: 73 (WT) or the K324A mutant variant thereof (SEQ ID NO: 74), to the Fc gamma receptor CD32B.

Figure 9:
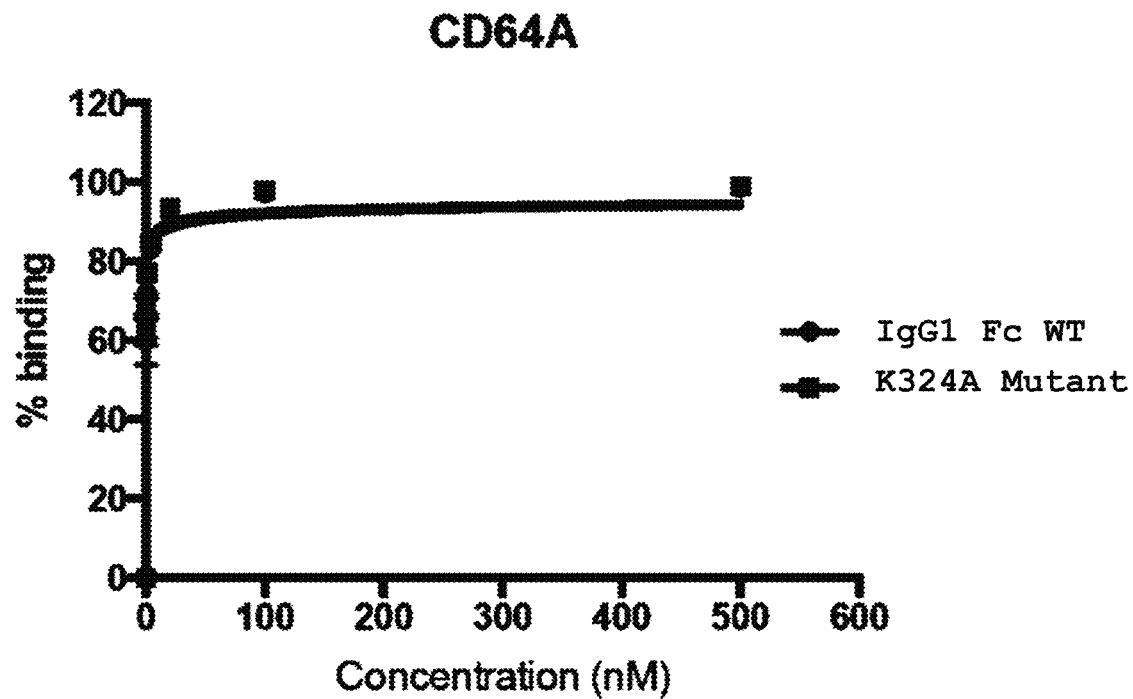

FIG. 9 shows the binding of two antibodies, which either comprise the human IgG1 Fc wild-type region of SEQ ID NO: 73 (WT) or the K324A mutant variant thereof (SEQ ID NO: 74), to the Fc gamma receptor CD64.

Figure 10:
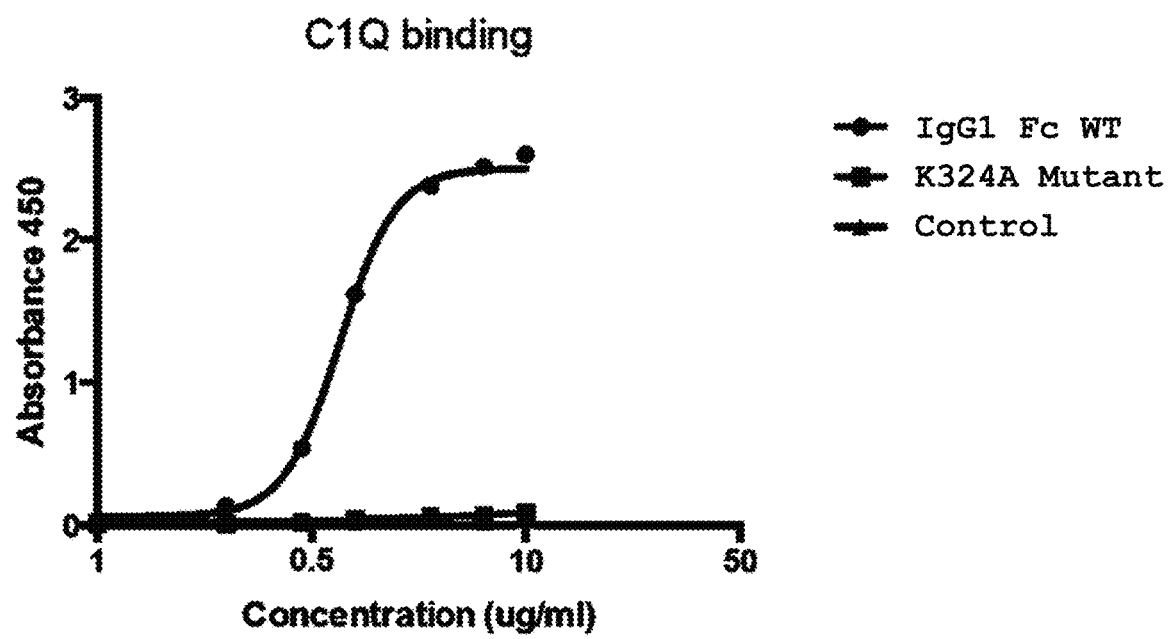

FIG. 10 shows the binding analysis of two antibodies, which either comprised the human IgG1 Fc wild-type region of SEQ ID NO: 73 (WT) or the K324A mutant variant thereof (SEQ ID NO: 74), to C1q.

DETAILED DESCRIPTION OF THE INVENTION

Definitions

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The antibody may be an IgM, IgG (e.g. IgG1, IgG2, IgG3 or IgG4), IgD, IgA or IgE, for example. Preferably however, the antibody is not an IgM antibody.

"Antibody fragments" comprise a portion of an intact antibody, generally the antigen binding or variable region of the intact antibody. Examples of antibody fragments include Fab, Fab', F(ab')2, and Fv fragments: diabodies; single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to "polyclonal antibody" preparations which typically include different antibodies directed against different determinants (epitopes), each monoclonal antibody is directed against a single determinant on the antigen. In addition to their specificity, the monoclonal antibodies can frequently be advantageous in that they are synthesized by the hybridoma culture, uncontaminated by other immunoglobulins. The "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler et al., Nature, 256:495 (1975), or may be made by generally well known recombinant DNA methods. The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are immunoglobulins, immunoglobulin chains or fragments thereof (such as Fv, Fab, Fab', F(ab')2 or other antigen-binding subsequences of antibodies) which contain a minimal sequence derived from a non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences.

These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986), Reichmann et al, Nature. 332:323-329 (1988): and Presta, Curr. Op. Struct. Biel., 2:593-596 (1992).

The term "therapeutically effective amount" as used herein and in the appended claims means that the amount of humanized antibody administered is of sufficient quantity to achieve the intended purpose, such as, in this case, the removal of circulating or soluble forms of pyroglutamated amyloid beta (Aβ N3pE) peptide and variants thereof.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Plickthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_D$) in the same polypeptide chain ($V_H$-$V_D$). By using a linker that is too short to allow pairing between the two domains on the same chain, the domains are forced to pair with the complementary domains of another chain and create two antigen-binding sites. Diabodies are described more fully in Hollinger et al., Proc. Natl. Acad. Sol. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

If peptide or amino acid sequences are mentioned herein, each amino acid residue is represented by a one-letter or a three-letter designation, corresponding to the trivial name of the amino acid, in accordance with the following conventional list:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The terms "a", "an" and "the" as used herein are defined to mean "one or more" and include the plural unless the context is inappropriate.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), sporadic Alzheimer's disease, Lewy body dementia, Down's syndrome, hereditary cerebral hemorrhage with amyloidosis (Dutch type); the Guam Parkinson-Dementia complex, familial forms of Alzheimer's disease like Familial British Dementia (FBD) and Familial Danish Dementia (FDD); as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes, and senile cardiac amyloidosis; and various eye diseases including macular degeneration, drusen-related optic neuropathy, and cataract due to beta-amyloid deposition.

"Amyloid R, Aβ or/β-amyloid" is an art recognized term and refers to amyloid β proteins and peptides, amyloid β precursor protein (APP), as well as modifications, fragments and any functional equivalents thereof. In particular, by amyloid β as used herein is meant any fragment produced by proteolytic cleavage of APP but especially those fragments which are involved in or associated with the amyloid pathologies including, but not limited to, $Aβ_{1-38}$, $Aβ_{1-40}$, $Aβ_{1-42}$. The amino acid sequences of these AP peptides are as follows:

Aβ 1-42 (SEQ ID NO. 1):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-Ile-Ala

Aβ 1-40 (SEQ ID NO. 2):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val

Aβ 1-38 (SEQ ID NO. 3):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly

"pGlu-Aβ" or "Aβ N3pE" refers to N-terminally truncated forms of Aβ, that start at the glutamic acid residue at position 3 in the amino acid sequence of Aβ, and wherein said glutamic acid residue is cyclized to form a pyroglutamic acid residue. In particular, by pGlu-Aβ or Aβ N3pE as used herein are meant those fragments which are involved in or associated with the amyloid pathologies including, but not limited to, pGlu-Aβ$_{3-38}$, pGlu-Aβ$_{3-40}$, p-Glu-Aβ$_{3-42}$.

The sequences of the N-terminally truncated forms of Aβ, Aβ$_{3-38}$, Aβ$_{3-40}$, Aβ$_{3-42}$ are as follows:

Aβ 3-42 (SEQ ID NO. 4):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val-Ile-Ala

Aβ 3-40 (SEQ ID NO. 5):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

Aβ 3-38 (SEQ ID NO. 6):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly

The present invention pertains to humanized antibodies specific for human Aβ peptides that are N-terminally truncated by cleaving off or loosing amino acids no. 1 and 2 of the N-terminus and in which the so uncovered N-terminal amino acid no. 3 is modified by pyroglutamate formation and which thus bear a pyroglutamate residue at position 3 of the N-terminus (further referred to as Aβ N3pE peptides or N3pE-Aβ peptides or pyroglutamated Aβ peptides).

In a first aspect, the present invention pertains to a humanized antibody, wherein the variable part of the light chain of said antibody comprises, consists essentially of or consists of an amino acid sequence of:

(SEQ ID NO: 7)
DVVMTQSPLSLPVTLGQPASISCKSSQSLLX$_1$SDGKTYLNWFQQRPGQSP

RRLX$_2$YLVSKLDSGVPDRFSGSGSGTDFTLKISRVEAEDVGVYYCVQGTH

FPFTFGGGTKVEIK, wherein
X$_1$ is selected from Y and H; and
X$_2$ is selected from A, I and T.

In a preferred embodiment of the present invention, the antibody having the variable part of the light chain of said antibody, which comprises, consists essentially of or consists of the amino acid sequence of SEQ ID NO: 7, comprises the following CDR regions in the light chain:

V$_L$ CDR1:
(SEQ ID NO: 8)
KSSQSLLX$_1$SDGKTYLN, wherein X$_1$ is selected from Y and H;

V$_L$ CDR2:
(SEQ ID NO: 9)
LVSKLDS;
and

V$_L$ CDR3:
(SEQ ID NO: 10)
VQGTHFP.

More preferably, in the variable part of the light chain of the antibody of the present invention, X$_1$ is Y and X$_2$ is I, and the variable part of the light chain thus comprises, consists essentially of or consists of the amino acid sequence of:

(SEQ ID NO: 11)
DVVMTQSPLSLPVTLGQPASISCKSSQSLLYSDGKTYLNWFQQRPGQSPR

RLIYLVSKLDSGVPDRFSGSGSGTDFTLKISRVEAEDVGVYYCVQGTHFP

FTFGGGTKVEIK.

In a preferred embodiment of the present invention, the antibody having the variable part of the light chain of said antibody, which comprises, consists essentially of or consists of the amino acid sequence of SEQ ID NO: 11, comprises the following CDR regions in the light chain:

V$_L$ CDR1:
(SEQ ID NO: 12)
KSSQSLLYSDGKTYLN,

V$_L$ CDR2:
(SEQ ID NO: 9)
LVSKLDS;
and

V$_L$ CDR3:
(SEQ ID NO: 10)
VQGTHFP.

Even preferably, in the variable part of the light chain of the antibody of the present invention, X$_1$ is Y and X$_2$ is A and the variable part of the light chain thus comprises, consists essentially of or consists of the amino acid sequence of:

(SEQ ID NO: 13)
DVVMTQSPLSLPVTLGQPASISCKSSQSLLYSDGKTYLNWFQQRPGQSPRR

LAYLVSKLDSGVPDRFSGSGSGTDFTLKISRVEAEDVGVYYCVQGTHFPFT

FGGGTKVEIK.

In a preferred embodiment of the present invention, the antibody having the variable part of the light chain of said antibody, which comprises, consists essentially of or consists of the amino acid sequence of SEQ ID NO: 13, comprises the CDR regions V$_L$ CDR1 of SEQ ID NO: 12, V$_L$ CDR2 SEQ ID NO: 9 and V$_L$ CDR3 of SEQ ID NO: 10.

Most preferably, in the variable part of the light chain of the antibody of the present invention, X$_1$ is Y and X$_2$ is T and the variable part of the light chain thus comprises, consists essentially of or consists of the amino acid sequence of:

(SEQ ID NO: 14)
DVVMTQSPLSLPVTLGQPASISCKSSQSLLYSDGKTYLNWFQQRPGQSPRR

LTYLVSKLDSGVPDRFSGSGSGTDFTLKISRVEAEDVGVYYCVQGTHFPFT

FGGGTKVEIK.

In a preferred embodiment of the present invention, the antibody having the variable part of the light chain of said antibody, which comprises, consists essentially of or consists of the amino acid sequence of SEQ ID NO: 14, comprises the CDR regions V$_L$ CDR1 of SEQ ID NO: 12, V$_L$ CDR2 SEQ ID NO: 9 and V$_L$ CDR3 of SEQ ID NO: 10.

Even most preferably, in the variable part of the light chain of the antibody of the present invention, $X_1$ is H and $X_2$ is T and the light chain thus comprises, consists essentially of or consists of the amino acid sequence of:

(SEQ ID NO: 15)
DVVMTQSPLSLPVTLGQPASISCKSSQSLLHSDGKTYLNWFQQRPGQSPRR

LTYLVSKLDSGVPDRFSGSGSGTDFTLKISRVEAEDVGVYYCVQGTHFPFT

FGGGTKVEIK.

In a preferred embodiment of the present invention, the antibody having the variable part of the light chain of said antibody, which comprises, consists essentially of or consists of the amino acid sequence of SEQ ID NO: 15, comprises the following CDR regions in the light chain:

$V_L$ CDR1:
(SEQ ID NO: 16)
KSSQSLLHSDGKTYLN, $V_L$ CDR2:
(SEQ ID NO: 9)
LVSKLDS;
and $V_L$ CDR3:
(SEQ ID NO: 10)
VQGTHFP.

Further in accordance with the first aspect, present invention pertains to a humanized antibody, wherein the variable part of heavy chain of said antibody comprises, consists essentially of or consists of an amino acid sequence of:

(SEQ ID NO: 17)
QVQLVQSGAEVKKSGASVKVSCKASGYSFTG$X_3$TMNWVRQAPGQGLEWMG

LINP$X_4$N$X_5$VTRYNQKF$X_6$GRVT$X_7X_8$RDTSTTTV$X_9$MELTSLTSEDTA $X_{10}$YYCTREAKREWDETYWGQGTLVTVSS;

wherein
$X_3$ is selected from Y and H;
$X_4$ is selected from Y and S;
$X_5$ is selected from G, T, A and E;
$X_6$ is selected from K and Q;
$X_7$ is selected from L and I;
$X_8$ is selected from I and T;
$X_9$ is selected from Y and H; and
$X_{10}$ is selected from V and T;

In a preferred embodiment of the present invention, the antibody having the variable part of the heavy chain of said antibody, which comprises, consists essentially of or consists of the amino acid sequence of SEQ ID NO: 17, comprises the following CDR regions in the heavy chain:

$V_H$ CDR1:
(SEQ ID NO: 18)
GYSFTG$X_3$TMN, wherein $X_3$ is selected from Y and H;

$V_H$ CDR2:
(SEQ ID NO: 19)
LINP$X_4$N$X_5$VTRYNQKF$X_6$G;

wherein $X_4$ is selected from Y and S, $X_5$ is selected from G, T, A and E and $X_6$ is selected from K and Q; and $V_H$ CDR3:
(SEQ ID NO: 20)
EAKREWDETY.

Preferably, in the variable part of the heavy chain of the antibody of the present invention, $X_3$ is Y, $X_4$ is Y, $X_5$ is G, $X_6$ is K, $X_7$ is T, $X_8$ is I, $X_9$ is Y and $X_{10}$ is V and the heavy chain thus comprises, consists essentially of or consists of the amino acid sequence of:

(SEQ ID NO: 21)
QVQLVQSGAEVKKSGASVKVSCKASGYSFTGYTMNWVRQAPGQGLEWMGL

INPYNGVTRYNQKFKGRVTLIRDTSTTTVYMELTSLTSEDTAVYYCTREA

KREWDETYWGQGTLVTVSS.

In a preferred embodiment of the present invention, the antibody having the variable part of the heavy chain of said antibody, which comprises, consists essentially of or consists of the amino acid sequence of SEQ ID NO: 21, comprises the following CDR regions in the heavy chain:

$V_H$ CDR1:
(SEQ ID NO: 22)
GYSFTGYTMN, $V_H$ CDR2:
(SEQ ID NO: 23)
LINPYNGVTRYNQKFKG;

$V_H$ CDR3:
(SEQ ID NO: 20)
EAKREWDETY.

More preferably, in the variable part of the heavy chain of the antibody of the present invention, $X_3$ is H, $X_4$ is S, $X_5$ is G, $X_6$ is Q, $X_7$ is I, $X_8$ is T, $X_9$ is H and $X_{10}$ is V and the heavy chain thus comprises, consists essentially of or consists of the amino acid sequence of:

(SEQ ID NO: 24)
QVQLVQSGAEVKKSGASVKVSCKASGYSFTGHTMNWVRQAPGQGLEWMGL

INPSNGVTRYNQKFQGRVTITRDTSTTTVHMELTSLTSEDTAVYYCTREA

KREWDETYWGQGTLVTVSS.

In a preferred embodiment of the present invention, the antibody having the variable part of the heavy chain of said antibody, which comprises, consists essentially of or consists of the amino acid sequence of SEQ ID NO: 24, comprises the following CDR regions in the heavy chain:

$V_H$ CDR1:
(SEQ ID NO: 25)
GYSFTGHTMN, $V_H$ CDR2:
(SEQ ID NO: 26)
LINPSNGVTRYNQKFQG;

$V_H$ CDR3:
(SEQ ID NO: 20)
EAKREWDETY.

Even more preferably, in the variable part of the heavy chain of the antibody of the present invention, $X_3$ is H, $X_4$ is S, $X_5$ is G, $X_6$ is Q, $X_7$ is I, $X_8$ is T, $X_9$ is H and $X_{10}$ is T and the heavy chain thus comprises, consists essentially of or consists of the amino acid sequence of:

(SEQ ID NO: 27)
QVQLVQSGAEVKKSGASVKVSCKASGYSFTGHTMNWVRQAPGQGLEWMGL

INPSNGVTRYNQKFQGRVTITRDTSTTTVHMELTSLTSEDTATYYCTREA

KREWDETYWGQGTLVTVSS.

In a preferred embodiment of the present invention, the antibody having the variable part of the heavy chain of said antibody, which comprises, consists essentially of or consists of the amino acid sequence of SEQ ID NO: 27, comprises the following CDR regions in the heavy chain:

$V_H$ CDR1:
(SEQ ID NO: 25)
GYSFTGHTMN, $V_H$ CDR2:
(SEQ ID NO: 26)
LINPSNGVTRYNQKFQG;

$V_H$ CDR3:
(SEQ ID NO: 20)
EAKREWDETY.

Most preferably, in the variable part of the heavy chain of the antibody of the present invention, $X_3$ is H, $X_4$ is S, $X_5$ is T, $X_6$ is Q, $X_7$ is I, $X_8$ is T, $X_9$ is H and $X_{10}$ is T and the heavy chain thus comprises, consists essentially of or consists of the amino acid sequence of:

(SEQ ID NO: 66)
QVQLVQSGAEVKKSGASVKVSCKASGYSFTGHTMNVWRQAPGQGLEWMGL

INPSNTVTRYNQKFQGRVTITRDTSTTTVHMELTSLTSEDTATYYCTREA

KREWDETYWGQGTLVTVSS.

In a preferred embodiment of the present invention, the antibody having the variable part of the heavy chain of said antibody, which comprises, consists essentially of or consists of the amino acid sequence of SEQ ID NO: 66, comprises the following CDR regions in the heavy chain:

$V_H$ CDR1:
(SEQ ID NO: 25)
GYSFTGHTMN, $V_H$ CDR2:
(SEQ ID NO: 67)
LINPSNTVTRYNQKFQG;

$V_H$ CDR3:
(SEQ ID NO: 20)
EAKREWDETY.

Even most preferably, in the variable part of the heavy chain of the antibody of the present invention, $X_3$ is H, $X_4$ is S, $X_5$ is A, $X_6$ is Q, $X_7$ is I, $X_8$ is T, $X_9$ is H and $X_{10}$ is T and the heavy chain thus comprises, consists essentially of or consists of the amino acid sequence of:

(SEQ ID NO: 68)
QVQLVQSGAEVKKSGASVKVSCKASGYSFTGHTMNWVRQAPGQGLEWMGL

INPSNAVTRYNQKFQGRVTITRDTSTTTVHMELTSLTSEDTATYYCTREA

KREWDETYWGQGTLVTVSS.

In a preferred embodiment of the present invention, the antibody having the variable part of the heavy chain of said antibody, which comprises, consists essentially of or consists of the amino acid sequence of SEQ ID NO: 68, comprises the following CDR regions in the heavy chain:

$V_H$ CDR1:
(SEQ ID NO: 25)
GYSFTGHTMN, $V_H$ CDR2:
(SEQ ID NO: 69)
LINPSNAVTRYNQKFQG;

$V_H$ CDR3:
(SEQ ID NO: 20)
EAKREWDETY.

Even most preferably, in the variable part of the heavy chain of the antibody of the present invention, $X_3$ is H, $X_4$ is S, $X_5$ is E, $X_6$ is Q, $X_7$ is I, $X_8$ is T, $X_9$ is H and $X_{10}$ is T and the heavy chain thus comprises, consists essentially of or consists of the amino acid sequence of:

(SEQ ID NO: 70)
QVQLVQSGAEVKKSGASVKVSCKASGYSFTGHTMNVWRQAPGQGLEWMG

LINPSNEVTRYNQKFQGRVTITRDTSTTTVHMELTSLTSEDTATYYCTR

EAKREWDETYWGQGTLVTVSS.

In a preferred embodiment of the present invention, the antibody having the variable part of the heavy chain of said antibody, which comprises, consists essentially of or consists of the amino acid sequence of SEQ ID NO: 70, comprises the following CDR regions in the heavy chain:

$V_H$ CDR1:
(SEQ ID NO: 25)
GYSFTGHTMN, $V_H$ CDR2:
(SEQ ID NO: 71)
LINPSNEVTRYNQKFQG;

$V_H$ CDR3:
(SEQ ID NO: 20)
EAKREWDETY.

Further according to first aspect of the invention, the humanized antibodies comprising, essentially consisting of or consisting of the following combinations of the variable parts of the light chain and heavy chain are preferred:

| Humanized antibody variant | Light chain variable part, SEQ ID NO: | Heavy chain variable part, SEQ ID NO: |
|---|---|---|
| General | 7 | 17 |
| i) | 11 | 21 |
| ii) | 11 | 24 |
| iii) | 11 | 27 |
| iv) | 11 | 66 |
| v) | 11 | 68 |
| vi) | 11 | 70 |
| vii) | 13 | 21 |
| viii) | 13 | 24 |
| ix) | 13 | 27 |
| x) | 13 | 66 |
| xi) | 13 | 68 |
| xii) | 13 | 70 |
| xiii) | 14 | 21 |
| xiv) | 14 | 24 |
| xv) | 14 | 27 |
| Xvi | 14 | 66 |
| Xvii | 14 | 68 |

| Humanized antibody variant | Light chain variable part, SEQ ID NO: | Heavy chain variable part, SEQ ID NO: |
| --- | --- | --- |
| Xviii | 14 | 70 |
| xix) | 15 | 21 |
| xx) | 15 | 24 |
| xxi) | 15 | 27 |
| Xxii | 15 | 66 |
| Xxiii | 15 | 68 |
| Xiv | 15 | 70 |

More preferably, the variable part of the light chain of the humanized antibody according to the invention comprises, consists essentially of or consists of the amino acid sequence of SEQ ID NO: 14.

Even more preferably, the variable part of the heavy chain of the humanized antibody according to the invention comprises, consists essentially of or consists of the amino acid sequence of SEQ ID NO: 27.

Even more preferably, the variable part of the heavy chain of the humanized antibody according to the invention comprises, consists essentially of or consists of the amino acid sequence selected from SEQ ID NO: 66, 72 and 74.

Most preferably, the variable part of the heavy chain of the humanized antibody according to the invention comprises, consists essentially of or consists of the amino acid sequence of SEQ ID NO: 70.

Most preferably, the variable part of the light chain of the humanized antibody according to the invention comprises, consists essentially of or consists of the amino acid sequence of SEQ ID NO: 14 and the variable part of the heavy chain of the humanized antibody according to the invention comprises, consists essentially of or consists of the amino acid sequence of SEQ ID NO: 27.

Even most preferably,
the variable part of the light chain of the humanized antibody according to the invention comprises, consists essentially of or consists of the amino acid sequence of SEQ ID NO: 14; and
the variable part of the heavy chain of the humanized antibody according to the invention comprises, consists essentially of or consists of the amino acid sequence of SEQ ID NO: 27; and
the variable part of the light chain of said antibody, which comprises, consists essentially of or consists of the amino acid sequence of SEQ ID NO: 14, comprises the CDR regions $V_L$ CDR1 of SEQ ID NO: 12, $V_L$ CDR2 SEQ ID NO: 9 and $V_L$ CDR3 of SEQ ID NO: 10; and
the variable part of the heavy chain of said antibody, which comprises, consists essentially of or consists of the amino acid sequence of SEQ ID NO: 27, comprises the CDR regions $V_H$ CDR1 of SEQ ID NO: 25, $V_H$ CDR2 SEQ ID NO: 26 and $V_H$ CDR3 of SEQ ID NO: 20.

Even most preferably, the variable part of the light chain of the humanized antibody according to the invention comprises, consists essentially of or consists of the amino acid sequence of SEQ ID NO: 14 and the variable part of the heavy chain of the humanized antibody according to the invention comprises, consists essentially of or consists of the amino acid sequence of SEQ ID NO: 70.

Even most preferably,
the variable part of the light chain of the humanized antibody according to the invention comprises, consists essentially of or consists of the amino acid sequence of SEQ ID NO: 14; and
the variable part of the heavy chain of the humanized antibody according to the invention comprises, consists essentially of or consists of the amino acid sequence of SEQ ID NO: 70; and
the variable part of the light chain of said antibody, which comprises, consists essentially of or consists of the amino acid sequence of SEQ ID NO: 14, comprises the CDR regions $V_L$ CDR1 of SEQ ID NO: 12, $V_L$ CDR2 SEQ ID NO: 9 and $V_L$ CDR3 of SEQ ID NO: 10; and
the variable part of the heavy chain of said antibody, which comprises, consists essentially of or consists of the amino acid sequence of SEQ ID NO: 70, comprises the CDR regions $V_H$ CDR1 of SEQ ID NO: 25, $V_H$ CDR2 SEQ ID NO: 71 and $V_H$ CDR3 of SEQ ID NO: 20.

In a second aspect, the present invention pertains to a humanized antibody, wherein the variable part of the light chain of said antibody comprises, consists essentially of or consists of an amino acid sequence of:

(SEQ ID NO: 28)
DIQMTQSPSSLSASVGDRVTITCRSSQSLVHSDGNTYLHWYQQKPGKAPK

LLIYKVSNRFSGVPSRFSGSGSGTDFTLTISSLQPEDFATYYCSQSTHVP

PTFGQGTKVEIK.

In a preferred embodiment of the present invention, the antibody having the variable part of the light chain of said antibody, which comprises, consists essentially of or consists of the amino acid sequence of SEQ ID NO: 28, comprises the following CDR regions in the light chain:

$V_L$ CDR1:
(SEQ ID NO: 29)
RSSQSLVHSDGNTYLH, $V_L$ CDR2:
(SEQ ID NO: 30)
KVSNRFS;
and $V_L$ CDR3:
(SEQ ID NO: 31)
SQSTHVPPT.

Further in accordance with the second aspect, the present invention pertains to a humanized antibody, wherein the variable part of the heavy chain of said antibody comprises, consists essentially of or consists of an amino acid sequence of:

(SEQ ID NO: 32)
EVQLVESGGGLVQPGGSLRLSCAASGFTFSDYGMAWVRQAPGKGLEWVSF

ISNLAYSIYYADTVTGRFTISRDNAKNSLYLQMNSLRAEDTAVYYCARYD

YDNILDYVMDYWGQGTLVTVSS.

In a preferred embodiment of the present invention, the antibody having the variable part of the heavy chain of said antibody, which comprises, consists essentially of or consists of the amino acid sequence of SEQ ID NO: 32, comprises the following CDR regions in the heavy chain:

$V_H$ CDR1:
(SEQ ID NO: 33)
GFTFSDYGMA,

-continued

V<sub>H</sub> CDR2:
FISNLAYSIYYADTVTG; (SEQ ID NO: 34)

V<sub>H</sub> CDR3:
YDYDNILDYVMDY. (SEQ ID NO: 35)

In a third aspect, the present invention pertains to a humanized antibody, wherein the variable part of the light chain of said antibody comprises, consists essentially of or consists of an amino acid sequence of:

(SEQ ID NO: 36)
DVVMTQSPLSLPVTLGQPASISCKSSQSLLYSNGKTYLNWFQQRPGQSPR

RLIYVVSKLDSGVPDRFSGSGSGTDFTLKISRVEAEDVGVYYCVQGTHFP

FTFGGGTKVEIK.

In a preferred embodiment of the present invention, the antibody having the variable part of the light chain of said antibody, which comprises, consists essentially of or consists of the amino acid sequence of SEQ ID NO: 36, comprises the following CDR regions in the light chain:

V<sub>L</sub> CDR1:
KSSQSLLYSNGKTYLN, (SEQ ID NO: 37)

V<sub>L</sub> CDR2:
VVSKLDS; (SEQ ID NO: 38)
and

V<sub>L</sub> CDR3:
VQGTHFPFT. (SEQ ID NO: 39)

Further in accordance with the third aspect, the present invention pertains to a humanized antibody, wherein the variable part of the heavy chain of said antibody comprises, consists essentially of or consists of an amino acid sequence of:

(SEQ ID NO: 40)
QVQLVESGAEVKKPGASVKVSCKASGYIFNNYWINWVRQAPGQGLEWMGQ

IYPGDGDTNYNGKFKGRVTITADESTSTAYMELSSLRSEDTAVYYCAREG

YIVYWGQGTLVTVSS.

In a preferred embodiment of the present invention, the antibody having the variable part of the heavy chain of said antibody, which comprises, consists essentially of or consists of the amino acid sequence of SEQ ID NO: 40, comprises the following CDR regions in the heavy chain:

V<sub>H</sub> CDR1:
GYIFNNY, (SEQ ID NO: 41)

V<sub>H</sub> CDR2:
QIYPGDGDTNYNGKFKG; (SEQ ID NO: 42)

V<sub>H</sub> CDR3:
EGYIVY. (SEQ ID NO: 43)

In a further particularly preferred embodiment, the present invention pertains to humanized antibodies specific for human N3pE-Aβ peptides, which comprise CDR regions in the light chain selected from:

| V<sub>L</sub> CDR1 | V<sub>L</sub> CDR 2 | V<sub>L</sub> CDR 3 |
|---|---|---|
| KSSQSLLHSDGKTYLN (SEQ ID NO: 16) | LVSKLDS (SEQ ID NO: 9) | VQGTHFP (SEQ ID NO: 10) |
| RSSQSLVHSDGNTYLH (SEQ ID NO: 29) | KVSNRFS (SEQ ID NO: 30) | SQSTHVPPT (SEQ ID NO: 31) |
| KSSQSLLYSNGKTYLN (SEQ ID NO: 37) | VVSKLDS (SEQ ID NO: 38) | VQGTHFPFT (SEQ ID NO: 39) |

Furthermore, the present invention pertains to human antibodies specific for human N3pE-Aβ peptides, which comprise CDR regions in the heavy chain selected from:

| V<sub>H</sub> CDR 1 | V<sub>H</sub> CDR 2 | V<sub>H</sub> CDR 3 |
|---|---|---|
| GYSFTGYTMN (SEQ ID NO: 22) | LINPYNGVTRYNQKFKG (SEQ ID NO: 23) | EAKREWDETY (SEQ ID NO: 20) |
| GYSFTGHTMN (SEQ ID NO: 25) | LINPSNGVTRYNQKFQG (SEQ ID NO: 26) | YDYDNILDYVMDY (SEQ ID NO: 35) |
| GFTFSDYGMA (SEQ ID NO: 33) | FISNLAYSIYYADTVTG (SEQ ID NO: 34) | EGYIVY (SEQ ID NO: 43) |
| GYIFNNY (SEQ ID NO: 41) | QIYPGDGDTNYNGKFKG (SEQ ID NO: 42) | |
| | LINPSNTVTRYNQKFQG (SEQ ID NO: 67) | |
| | LINPSNAVTRYNQKFQG (SEQ ID NO: 69) | |
| | LINPSNEVTRYNQKFQG (SEQ ID NO: 71) | |

Preferred humanized antibodies according to the invention are humanized forms of monoclonal mouse antibodies that are produced by a hybridoma cell line selected from:

| Aβ 5-5-6 | (Deposit No. DSM ACC 2923) |
| Aβ 6-1-6 | (Deposit No. DSM ACC 2924) |
| Aβ 17-4-3 | (Deposit No. DSM ACC 2925) |
| Aβ 24-2-3 | (Deposit No. DSM ACC 2926) | which are described in WO 2010/009987.

The sequences of the light and heavy chains for the humanized antibodies of the present invention can vary. The immunoglobulins can have two pairs of light chain/heavy chain complexes, at least one chain comprising one or more mouse complementarity determining regions (CDRs) functionally joined to human framework region segments.

In another embodiment, the present invention is directed to recombinant polynucleotides encoding the humanized antibodies of the invention comprising the heavy and light chain CDRs as set forth herein.

The human framework region of the antibodies of the invention is determined by comparison of a framework or variable region amino acid sequence of a CDR-providing non-human immunoglobulin with corresponding sequences in a sequence collection comprising human immunoglobulin variable regions. A sequence having a high percentage of identical amino acids is selected.

Preferred polynucleotides of the present invention encode antibodies, comprising CDRs selected from those consisting of the amino acid sequences of SEQ ID NOs: 9, 10, 16, 29-31 and 37-39 in the light chain and selected from those consisting of the amino acid sequences of SEQ ID NOs: 20, 22, 23, 25, 26, 33-35, 41-43, 67, 69 and 71 in the heavy chain.

Further preferred are polynucleotides, which encode antibodies, wherein the variable part of the light chain comprises, essentially consists or consists of an amino acid sequence selected from SEQ ID NOs: 7, 11, 13, 14, and 28.

Even preferred are polynucleotides, which encode antibodies, wherein the variable part of the heavy chain comprises, essentially consists or consists of an amino acid sequence selected from SEQ ID NOs: 17, 21, 24, 27, 32, 36, 40, 66, 68 and 70.

In a further embodiment, the humanized antibodies of the present invention have a human IgG1 Fc region, which comprises, consists essentially of or consists of an amino acid sequence of SEQ ID NO: 73.

C1q and two serine proteases, C1r and C1s, form the complex C1, the first component of the complement dependent cytotoxicity (CDC) pathway. C1q is a hexavalent molecule with a molecular weight of approximately 460,000 and a structure likened to a bouquet of tulips in which six collagenous "stalks" are connected to six globular head regions (Burton and Woof, Advances in Immunol 51:1-84; 1992). Binding of IgG1 molecules to C1q initiates complement activation and subsequently leads to complement-mediated cell lysis. The humanized antibodies of the present invention shall be used in treatment of inflammatory diseases and conditions, i.e. the humanized antibodies of the present invention shall have anti-inflammatory properties.

Effector functions of the humanized antibodies of the invention can also be mediated by the interaction of the Fc region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysing of erythrocytes and various other cellular targets (e.g. tumor cells) coated with the corresponding antibody, via antibody dependent cell mediated cytotoxicity (ADCC) (Van de Winkel and Anderson, J. Leuk. Bioi. 49:511-24; 1991).

Therefore, the present invention further provides humanized antibodies that still bind to the Fc receptors to fulfill their effector functions. But, preferably the humanized antibodies of the invention do not show a complement dependent cytotoxicity. More preferably, the humanized antibodies of the invention do not activate the complement system, but rather inhibit the complement-mediated cell lysis.

Thus, in a preferred embodiment, the humanized antibodies of the present invention have a human IgG Fc region, which comprises one or more an amino acid substitutions, preferably the substitution of 3 or 2 amino acids, most preferably the substitution of one amino acid. The amino acid substitutions can be achieved by conventional methods, such as site-directed mutagenesis of the human IgG1 Fc region of the antibodies of the present invention.

In a more preferred embodiment, the humanized antibodies of the present invention have a human IgG Fc region which comprises an amino acid substitution at position 324 as shown in SEQ ID NO: 74 [position 324 corresponds to position 322 according to EU numbering scheme, Kabat et al., Sequences of Proteins of Immunological Interest, 5th Ed., US Department of Health and Human Services, NIH Publication No. 91-3242, National Institutes of Health, Bethesda, Md. (1991); Edelman et al., PNAS USA 63:78-85 (1969)]. The amino acid substitution is preferably K324A.

In a most preferred embodiment, the humanized antibodies of the present invention have a human IgG Fc region, which comprises, consists essentially of or consists of an amino acid sequence of SEQ ID NO: 74.

Further most preferably, the variable part of the light chain of the humanized antibody according to the invention comprises, consists essentially of or consists of the amino acid sequence of SEQ ID NO: 14; and the variable part of the heavy chain of the humanized antibody according to the invention comprises, consists essentially of or consists of the amino acid sequence of SEQ ID NO: 27; and the human IgG Fc region comprises, consists essentially of or consists of the amino acid sequence of SEQ ID NO: 74.

Even most preferably,
the variable part of the light chain of the humanized antibody according to the invention comprises, consists essentially of or consists of the amino acid sequence of SEQ ID NO: 14; and
the variable part of the heavy chain of the humanized antibody according to the invention comprises, consists essentially of or consists of the amino acid sequence of SEQ ID NO: 27; and
the human IgG Fc region comprises, consists essentially of or consists of the amino acid sequence of SEQ ID NO: 74;
the variable part of the light chain of said antibody, which comprises, consists essentially of or consists of the amino acid sequence of SEQ ID NO: 14, comprises the CDR regions $V_L$ CDR1 of SEQ ID NO: 12, $V_L$ CDR2 SEQ ID NO: 9 and $V_L$ CDR3 of SEQ ID NO: 10; and
the variable part of the heavy chain of said antibody, which comprises, consists essentially of or consists of the amino acid sequence of SEQ ID NO: 27, comprises the CDR regions $V_H$ CDR1 of SEQ ID NO: 25, $V_H$ CDR2 SEQ ID NO: 26 and $V_H$ CDR3 of SEQ ID NO: 20.

Even most preferably, the variable part of the light chain of the humanized antibody according to the invention comprises, consists essentially of or consists of the amino acid sequence of SEQ ID NO: 14; and the variable part of the heavy chain of the humanized antibody according to the invention comprises, consists essentially of or consists of the amino acid sequence of SEQ ID NO: 70; and the human IgG Fc region comprises, consists essentially of or consists of the amino acid sequence of SEQ ID NO: 74.

Even most preferably,
the variable part of the light chain of the humanized antibody according to the invention comprises, consists essentially of or consists of the amino acid sequence of SEQ ID NO: 14; and
the variable part of the heavy chain of the humanized antibody according to the invention comprises, consists essentially of or consists of the amino acid sequence of SEQ ID NO: 70; and
the human IgG Fc region comprises, consists essentially of or consists of the amino acid sequence of SEQ ID NO: 74;
the variable part of the light chain of said antibody, which comprises, consists essentially of or consists of the amino acid sequence of SEQ ID NO: 14, comprises the CDR regions $V_L$ CDR1 of SEQ ID NO: 12, $V_L$ CDR2 SEQ ID NO: 9 and $V_L$ CDR3 of SEQ ID NO: 10; and
the variable part of the heavy chain of said antibody, which comprises, consists essentially of or consists of the amino acid sequence of SEQ ID NO: 70, comprises the CDR regions V$_H$ CDR1 of SEQ ID NO: 25, V$_H$ CDR2 SEQ ID NO: 71 and V$_H$ CDR3 of SEQ ID NO: 20.

Preferred polynucleotides of the present invention encode antibodies, comprising CDRs selected from those consisting of the amino acid sequences of SEQ ID NOs: 9, 10, 16, 29-31 and 37-39 in the light chain and selected from those consisting of the amino acid sequences of SEQ ID NOs: 20, 22, 23, 25, 26, 33-35, 41-43, 67, 69 and 71 in the heavy chain; and comprising a human IgG Fc region selected from SEQ ID NOs: 73 and 74.

Further preferred are polynucleotides, which encode antibodies, wherein the variable part of the light chain comprises, essentially consists or consists of an amino acid sequence selected from SEQ ID NOs: 7, 11, 13, 14, and 28; and wherein the human IgG Fc region comprises, consists essentially of or consists of an amino acid sequence selected from SEQ ID NO: 73 or 74.

Even preferred are polynucleotides, which encode antibodies, wherein the variable part of the heavy chain comprises, essentially consists or consists of an amino acid sequence selected from SEQ ID NOs: 17, 21, 24, 27, 32, 36, 40, 66, 68 and 70; and wherein the human IgG Fc region comprises, consists essentially of or consists of an amino acid sequence selected from SEQ ID NO: 73 or 74.

The aforementioned polynucleotides can be integrated into expression vectors well known in the art. Transfection of these expression vectors in an appropriate host, the selection of the host as well as the expression collection and purification of the light chains, heavy chains, light/heavy chain dimers or intact antibodies, binding fragments or other immunoglobulin forms are well-known procedures in the art.

One skilled in the art can select a vector based on desired properties, for example, for production of a vector in a particular cell such as a mammalian cell or a bacterial cell.

Any of a variety of inducible promoters or enhancers can be included in the vector for expression of an antibody of the invention or nucleic acid that can be regulated. Such inducible systems, include, for example, tetracycline inducible System (Gossen & Bizard, Proc. Natl. Acad. Sci. USA, 89:5547-5551 (1992); Gossen et al., Science, 268:17664769 (1995); Clontech, Palo Alto, Calif.); metallothionein promoter induced by heavy metals; insect steroid hormone responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); mouse mammary tumor virus (MMTV) induced by steroids such as glucocorticoid and estrogen (Lee et al., Nature, 294:228-232 (1981); and heat shock promoters inducible by temperature changes; the rat neuron specific enolase gene promoter (Forss-Petter, et al., Neuron 5; 197-197 (1990)); the human β-actin gene promoter (Ray, et al., Genes and Development (1991) 5:2265-2273); the human platelet derived growth factor B (PDGF-B) chain gene promoter (Sasahara, et al., Cell (1991) 64:217-227); the rat sodium channel gene promoter (Maue, et al., Neuron (1990) 4:223-231); the human copper-zinc superoxide dismutase gene promoter (Ceballos-Picot, et al., Brain Res. (1991) 552:198-214); and promoters for members of the mammalian POU-domain regulatory gene family (Xi et al., (1989) Nature 340:35-42).

Regulatory elements, including promoters or enhancers, can be constitutive or regulated, depending upon the nature of the regulation. The regulatory sequences or regulatory elements are operatively linked to one of the polynucleotide sequences of the invention such that the physical and functional relationship between the polynucleotide sequence and the regulatory sequence allows transcription of the polynucleotide sequence. Vectors useful for expression in eukaryotic cells can include, for example, regulatory elements including the CAG promoter, the SV40 early promoter, the cytomegalovirus (CMV) promoter, the mouse mammary tumor virus (MMTV) steroid-inducible promoter, Pgtf, Moloney marine leukemia virus (MMLV) promoter, thy-1 promoter and the like.

If desired, the vector can contain a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999)) and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al, supra, (1999); U.S. Pat. No. 5,981,830). DNA constructs of the invention can incorporate a positive selectable marker, a negative selectable marker, or both (see, for example, U.S. Pat. No. 5,981,830). Various mammalian cell culture systems can also be employed to express a recombinant protein. Examples of mammalian expression systems include the COS-7 lines of monkey kidney fibroblasts, described by Gluzman, Cell, 23: 175 (1981). Other cell lines capable of expressing a compatible vector include, for example, the C127, 3T3, CHO, HeLa and BHK cell lines. Mammalian expression vectors will generally comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Recovery can be facilitated if the polypeptide is expressed at the surface of the cells, but such is not a prerequisite. Recovery may also be desirable of cleavage products that are cleaved following expression of a longer form of the polypeptide. Protein refolding steps as known in this art can be used, as necessary, to complete configuration of the mature protein. High performance liquid chromatography (HPLC) can be employed for final purification steps.

Human constant region DNA sequences can be isolated in accordance with well-known procedures from a variety of human cells.

The present invention pertains in particular to humanized antibodies which are characterized in that they bind to Aβ N3pE peptides with a high affinity. The present invention also pertains to antibodies which are characterized in that they bind to Aβ N3pE peptides or immunologically active fragments thereof with a high affinity. Said high affinity means in the context of the present invention an affinity of a $K_D$ value of $10^{-5}$ M, $10^{-6}$ M or $10^{-7}$ M or better, preferably a $K_D$ value of $10^{-8}$ M or better, and even more preferably a $K_D$ value of $10^{-9}$ M–$10^{-12}$ M. Thereby, the inventive antibodies bind to monomeric Aβ N3pE with a higher affinity than previously known antibodies.

Preferably, the binding epitope of the humanized antibodies of the present invention in Aβ N3pE binds is an epitope, which carries a pyroglutamate at the N-terminus. More preferably, the binding epitope of the humanized antibody of the invention is selected from the group consisting of pEFRHDSGYEVHHQKLV, (SEQ ID NO: 50)

pEFRHDSGYEVHHQKL, (SEQ ID NO: 54)

pEFRHDSGYEVHHQK, (SEQ ID NO: 55)

pEFRHDSGYEVHHQ, (SEQ ID NO: 56)

pEFRHDSGYEVHH, (SEQ ID NO: 57)

pEFRHDSGYEVH, (SEQ ID NO: 58)

pEFRHDSGYEV, (SEQ ID NO: 59)

pEFRHDSGYE, (SEQ ID NO: 60)

pEFRHDSGY, (SEQ ID NO: 61)

pEFRHDSG, (SEQ ID NO: 62)

pEFRHDS, (SEQ ID NO: 63)

pEFRHD, (SEQ ID NO: 72)

pEFRH, (SEQ ID NO: 64)
and pEFR. (SEQ ID NO: 65)

Most preferably, the humanized antibodies of the invention do not bind to binding epitopes that do not carry a pyroglutamate at the N-terminus.

Even most preferably, when binding to the aforementioned and subsequently mentioned binding epitopes, the humanized antibodies of the invention always bind to sequences or parts of sequences, which contain the pyroglutamate at the N-terminus. The humanized antibodies of the invention do not bind to sequences or parts of sequences, which do not contain the pyroglutamate at the N-terminus.

Further, the humanized antibody of the invention can also bind to an Aβ N3pE variant.

In the context of the present invention, an Aβ N3pE variant is in particular pE-Aβ$_{3-38}$,
pE-Aβ$_{3-40}$,
pE-Aβ$_{3-42}$ Further variants of Aβ N3pE peptides are all Aβ N3pE variants, which have been shown to accumulate in the brain as a consequence of Alzheimer's disease or preceding Alzheimer's disease. These are the pE-Aβ$_{3-x}$ peptides, wherein x is defined as an integer having a value in the range of 19 to 42, e.g. in the above pE-Aβ$_{3-42}$, "42" would be the integer for "x".

In the context of the present invention a "functional variant" of the inventive humanized antibody is an antibody which retains the binding capacities, in particular binding capacities with high affinity to a pE-Aβ$_{3-x}$ peptide. The provision of such functional variants is known in the art and encompasses the above-mentioned possibilities, which were indicated under the definition of antibodies and fragments thereof.

In a further embodiment, the humanized antibody is an antibody fragment, as defined above.

In a further preferred embodiment, the humanized antibody of the invention is a humanized antibody which has the complementarity-determining regions (CDRs) of the above-defined antibodies. Preferably, the antibody can be labeled; possible labels are those as mentioned above and all those known to a person skilled in the art of diagnostic uses of antibodies in particular.

In another embodiment, the humanized antibodies may be immobilized on a solid phase.

In another embodiment, the humanized antibodies according to the invention and as described herein before or a fragments thereof, exhibit a binding affinity to an Aβ N3pE oligomer, fiber, fibril or filament which is at least 2 times, particularly at least 4 times, particularly at least 10 times, particularly at least 15 times, more particularly at least 20 times, but especially at least 25 times higher than the binding affinity to an Aβ N3pE monomer.

In still another embodiment, humanized antibodies or fragments thereof are provided as described herein before, which substantially bind to aggregated Aβ, including Aβ plaques, which contain Aβ N3pE, in the mammalian, particularly the human brain but, preferably, do not show any significant cross-reactivity with amyloid precursor protein (APP).

In another aspect of the invention, humanized antibodies or fragments thereof are provided as described herein before, which antibodies substantially bind to oligomeric or polymeric amyloid, which contains Aβ N3pE, particularly amyloid β (Aβ) in the mammalian, particularly the human brain but, preferably, do not show any significant cross-reactivity with amyloid precursor protein (APP).

The present invention relates also to compositions comprising said humanized antibodies and the use of said compositions for the treatment of amyloidosis, especially for the treatment of neurodegenerative disease in a mammal, in particular in a human. Said neurodegenerative disease is in particular selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome. Preferably, said neurodegenerative disease is Alzheimer's disease.

Thus, in a preferred embodiment, the present invention is directed to a method of treating and/or preventing conditions characterized by the formation of plaques comprising Aβ N3pE in mammals, preferably in humans, which method comprises administering, preferably peripherally, to a human in need of such treatment a therapeutically or prophylactically effective amount of a humanized monoclonal antibody of the invention or a immunologically reactive fragment thereof, which antibody specifically binds to an epitope of the Aβ N3pE peptide that carries pyroglutamate at the N-terminus.

In another embodiment, the invention is directed to a method to inhibit the formation of amyloid plaques and to clear or remove amyloid plaques in mammals, preferably in humans, which method comprises administering to a human subject in need of such inhibition an effective amount of a humanized antibody that binds to Aβ N3pE in the circulation, body fluids or tissues, especially in the brain and further preferably, leads to the clearance of Aβ N3pE in plasma and the brain.

Accordingly, the invention also provides methods of reversing cognitive decline, improving cognition, treating cognitive decline, and preventing cognitive decline in a subject diagnosed with mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease comprising administering to the subject an effective amount of a humanized antibody of the invention.

The invention also provides the use of a humanized antibody of the invention for the manufacture of a medicament, for treating, preventing, or reversing mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease; or to reverse cognitive decline, improve cognition, treat cognitive decline, and prevent cognitive decline in a subject diagnosed with mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease.

The invention further provides the humanized antibodies disclosed herein for use in the prevention, treatment, or the reversion of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease; for treating, preventing, or the reversion of cognitive decline, improvement of cognition, treatment of cognitive decline, and prevention of cognitive decline in a subject diagnosed with mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome and clinical or pre-clinical cerebral amyloid angiopathy, preferably Alzheimer's disease; or the inhibition of the formation of an1yloid plaques or the effects of Aβ N3pE in mammals, preferably in humans.

In a specific embodiment the invention provides a method for retaining or increasing cognitive memory capacity but, particularly, for restoring the cognitive memory capacity of a mammal, particularly a human, suffering from memory impairment by administering to an animal, particularly a mammal or a human, a humanized antibody, or a pharmaceutical composition comprising a humanized antibody according to the invention and as described herein before.

The invention further provides methods to assess the response of a human subject to treatment with a humanized antibody that binds Aβ N3pE or a variant thereof, comprising:

a) administering a humanized antibody of the invention or a fragment thereof to the subject; and
b) measuring the concentration of AB N3pE in a biological sample taken from the subject.

The invention also provides a method of treating a human subject with an antibody that binds Aβ N3pE or a variant thereof, comprising:

a) administering a first amount of the antibody or fragment thereof to the subject;
b) within 3 hours to two weeks after administering the first dose, measuring the concentration of Aβ N3pE in a biological sample taken from the subject;
c) if necessary, calculating a second amount of antibody or fragment thereof based on the result of step b), which second amount is the same as or different than the first amount; and
d) administering the second amount of the antibody or fragment.

The invention also includes a method of assessing in a mammalian, preferably a human subject the efficacy of an antibody that binds to Aβ N3pE, or a fragment thereof, for inhibiting or preventing Aβ N3pE related amyloid plaque formation, for reducing the load of Aβ N3pE containing plaques, for reducing the effects of toxic Aβ N3pE and variants thereof, or for treating a condition or a disease associated with plaques containing Aβ N3pE, comprising:

a) obtaining a first biological sample form the subject;
b) measuring a baseline concentration of Aβ N3pE in the first sample;
c) administering a humanized antibody of the invention or fragment thereof to the subject;
d) within 3 hours to two weeks after administering the antibody or fragment thereof, obtaining a second biological sample from the subject; and
e) measuring the concentration of Aβ N3pE in the second biological sample; wherein, efficacy is related to the quantity of Aβ N3pE bound to the antibody in the blood and the concentration of Aβ N3pE, in particular the reduction of the concentration thereof, in the second biological sample compared to the first biological sample.

The biological sample may be any sample, for example from a human. In one specific example, the sample is a tissue sample, a body fluid sample or a cell sample. In one embodiment, the biological sample is selected from the group consisting of blood, serum, urine, cerebrospinal fluid (CSF), plasma, lymph, saliva, sweat, pleural fluid, synovial fluid, tear fluid, bile and pancreas secretion. In a further embodiment, the biological sample is plasma. In a preferred embodiment, the biological sample is CSF.

The biological sample can be obtained from a subject in a manner well-known to a person skilled in the art. In particular, a blood sample can be obtained from a subject and the blood sample can be separated into serum and plasma by conventional methods. The subject, from which the biological sample is obtained is preferably a subject suspected of being afflicted with a disease or condition of amyloidosis, preferably Alzheimer's disease, at risk of developing Alzheimer's disease and/or being at risk of or having any other kind of dementia.

In particular, the sample is obtained from a subject suspected of having Mild Cognitive Impairment (MCI) and/or being in the early stages of Alzheimer's disease.

The efficacy of the humanized antibodies of the invention in the diagnosis, prevention and/or treatment of amyloidosis, such as mild cognitive impairment, Alzheimer's Disease, Familial British Dementia or Familial Danish Dementia and, e.g. neurodegeneration in Down Syndrome can be tested in existing animal models of Alzheimer's disease.

Suitable animal models of Alzheimer's Disease are reviewed in McGowan et al. TRENDS in Genetics, Vol. 22, No. May 2006, pp 281-289, and are selected from PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP, 3xTgAD, as described below.

PDAPP: First mutant APP transgenic model with robust plaque pathology. Mice express a human APP cDNA with the Indiana mutation ($APP_{V717F}$). Plaque pathology begins between 6-9 months in hemizygous PDAPP mice. There is synapse loss but no overt cell loss and not NFT pathology is observed. This model has been used widely in vaccination therapy strategies.

Tg2576: Mice express mutant $APP_{SWE}$ under control of the hamster prion promoter. Plaque pathology is observed from 9 months of age. These mice have cognitive deficits but no cell loss or NFT pathology. This model is one of the most widely used transgenic models in the field of Alzheimer's disease.

APP23: Mice express mutant $APP_{SWE}$ under control of the Thy1 promoter. Prominent cerebrovascular amyloid, amyloid deposits are observed from 6 months of age and some hippocampal neuronal loss is associated with amyloid plaque formation.

TgCRND8: Mice express multiple APP mutations (Swedish plus Indiana). Cognitive deficits coincide with rapid extracellular plaque development at ~3 months of age. The cognitive deficits can be reversed by Aβ vaccination therapy.

$PSEN_{1M146V}$ or $PSEN_{1M146L}$ (lines 6.2 and 8.9, respectively): These models where the first demonstration in vivo that mutant PSEN1 selectively elevates Aβ42. No overt plaque pathology is observed.

PSAPP (Tg2576×$PSEN_{1M146L}$, PSEN1-A246E+$APP_{SWE}$): Bigenic transgenic mice, with the addition of the mutant PSEN1 transgene which markedly accelerated amyloid pathology compared with singly transgenic mutant APP mice, demonstrating that the PSEN1-driven elevation of Aβ 42 enhances plaque pathology.

$APP_{Dutch}$: Mice express APP with the Dutch mutation that causes hereditary cerebral hemorrhage with amyloidosis-Dutch type in humans. $APP_{Dutch}$ mice develop severe congophilic amyloid angiopathy. The addition of a mutant PSEN1 transgene redistributes the amyloid pathology to the parenchyma indicating differing roles for Aβ 40 and Aβ 42 in vascular and parenchymal amyloid pathology.

BRI-Aβ40 and BRI-Aβ42: Mice express individual Aβ isoforms without APP over-expression. Only mice expressing Aβ 42 develop senile plaques and CAA, whereas BRI-Aβ 40 mice do not develop plaques, suggesting that Aβ 42 is essential for plaque formation.

JNPL3: Mice express 4RON MAPT with the P301L mutation. This is the first transgenic model, with marked tangle pathology and cell loss, demonstrating that MAPT alone can cause cellular damage and loss. JNPL3 mice develop motor impairments with age owing to severe pathology and motor neuron loss in the spinal cord.

$Tau_{P301S}$: Tansgenic mice expressing the shortest isoform of 4R MAPT with the P301S mutation. Homozygous mice develop severe paraparesis at 5-6 months of age with widespread neurofibrillary pathology in the brain and spinal cord and neuronal loss in the spinal cord.

$TaU_{V337M}$: Low level synthesis of 4R MAPT with the V337M mutation (1/10 endogenous MAPT) driven by the promoter of platelet-derived growth factor (PDGF). The development of neurofibrillary pathology in these mice suggests the nature of the MAPT rather than absolute MAPT intracellular concentration drives pathology.

$Tau_{R406W}$: Mice expressing 4R human MAPT with the R406W mutation under control of the CAMKII promoter. Mice develop MAPT inclusions in the forebrain from 18 months of age and have impaired associative memory.

rTg4510: Inducible MAPT transgenic mice using the TET-off system. Abnormal MAPT pathology occurs from one month of age. Mice have progressive NFT pathology and severe cell loss. Cognitive deficits are evident from 2.5 months of age. Turning off the transgene improves cognitive performance but NT pathology worsens.

$H_{tau}$: Transgenic mice expressing human genomic MAPT only (mouse MAPT knocked-out). Htau mice accumulate hyperphosphorylated MAPT from 6 months and develop Thio-S-positive NFT by the time they are 15 months old.

TAPP (Tg2576×JNPL3): Increased MAPT forebrain pathology in TAPP mice compared with JNPL3 suggesting mutant APP and/or Aβ can affect downstream MAPT pathology. 3xTgAD: Triple transgenic model expressing mutant $APP_{SWE}$, $MAPT_{P301L}$ on a $PSEN1_{M146V}$ 'knock-in' background (PSNE1-KI). Mice develop plaques from 6 months and MAPT pathology from the time they are 12 months old, strengthening the hypothesis that APP or Aβ can directly influence neurofibrillary pathology.

Moreover, WO 2009/034158 discloses non-human transgenic animal models, wherein the transgene encodes at least one amyloid beta (Aβ) peptide selected from the group consisting of AβN3E-42, AβN3Q-42, AβN3E-40 and AβN3Q-40. These Aβ peptides are substrates of QC and QPCTL, resulting in the cyclization of the N-terminal glutamine (Q) or glutamate (N) to pyroglutamate (pGlu). Thus, these transgenic animal models provide a model system for the investigation of the effect of pGlu-Aβ peptides on the course of the development of neurodegenration.

Anti-Aβ pN3pE antibodies may also be useful in diagnostic assays for Aβ pN3pE, e.g. detecting its occurrence in specific cells, tissues, or serum. Thus, the humanized antibodies according to the present invention are especially useful in a diagnostic method to detect amyloidosis, in particular a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

For diagnostic applications, the antibody typically will be labelled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Gitigen et al., Ed., Wiley-lnterscience. New York, N.Y. Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, p hycoerythrin and Texas Red are available. The fluorescent labels can be conjugated to the antibody using the techniques disclosed in *Current Protocols in Immunology*, supra for example. Fluorescence can be quantified using a fluorimeter.

(c) Various enzyme-substrate labels are available. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g, firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase. 0-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym (ed Langone & H. Van Vunakis), Academic Press, New York, 73: 147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));

(ii) alkaline phosphatase (Aβ) with para-Nitrophenyl phosphate as chromogenic substrate; and (iii) β-D-galactosidase β-D-Gal) with a chromogenic substrate (e.g. p-nitrophenyl-β-D-galactosidase) or the fluorogenic substrate 4-methylumbelliferyl-β-D-galactosidase.

Numerous other enzyme-substrate combinations are available to those skilled in the art.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

The humanized antibodies of the present invention may be employed in any known assay method, such as competitive binding assays, direct and indirect sandwich assays, and immunoprecipitation assays. Zola, *Monoclonal Antibodies A Manual of Techniques*, pp. 147-158 (CRC Press. Inc., 1987)

Competitive binding assays rely on the ability of a labeled standard to compete with the test sample analyte for binding with a limited amount of antibody. The amount of Aβ N3pE in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one preferable type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

The present invention also relates to a composition which comprises the humanized antibodies as defined above, wherein said composition is a composition for a diagnostic use, especially for the diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; in particular by detection of Aβ N3pE or variants thereof in a biological sample.

Diagnostic Kits

As a matter of convenience, the antibody of the present invention can be provided in a kit, i.e., a packaged combination of reagents in predetermined amounts with instructions for performing the diagnostic assay. Where the antibody is labelled with an enzyme, the kit will include substrates and cofactors required by the enzyme (e.g. a substrate precursor which provides the detectable chromophore or fluorophore). In addition, other additives may be included such as stabilizers, buffers (e.g. a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The diagnostic kit according to the invention may contain a further biologically active substance as described below. Especially preferred for the use in the diagnostic kit as said further biologically active substance is an inhibitor of glutaminyl cyclase.

The diagnostic kit of the invention is especially useful for the detection and diagnosis of amyloid-associated diseases and conditions, in particular neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

The present invention also pertains to the humanized antibody of the invention or the composition comprising the humanized antibody, both as defined above, for use in an in vitro diagnostic method. In particular, this diagnostic method is directed to diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; especially by detecting an Aβ N3pE or variants thereof in a biological sample.

In a particularly preferred embodiment, the present invention pertains to the following method:
In vitro or in situ diagnostic method for the diagnosis of an amyloid-associated disease or condition, preferably Alzheimer's disease, comprising the following steps:
contacting a humanized antibody according to the invention with a sample, preferably selected from a serum, liquor or CSF sample, most preferably a serum sample; or a specific body part or body area of a subject suspected to be afflicted with said condition or disease, and
detecting binding of the antibody to Aβ N3pE, from the sample.

More particularly, the invention relates to a method of diagnosis of an amyloid-associated disease or condition, preferably Alzheimer's disease, comprising detecting the immunospecific binding of a humanized antibody of the invention or an immunologically active fragment thereof to Aβ N3pE, in a sample or in situ which includes the steps of
(a) bringing the sample or a specific body part or body area suspected to contain the amyloid protein into contact with a humanized antibody of the invention, or a fragment thereof;
(b) allowing the antibody and/or a functional part thereof, to bind to Aβ N3pE to form an immunological complex;
(c) detecting the formation of the immunological complex; and
(d) correlating the presence or absence of the immunological complex with the presence or absence of Aβ N3pE in the sample or specific body part or area.

Also comprised is a method of determining the extent of amyloidogenic plaque burden in a tissue and/or body fluids comprising
(a) obtaining a sample representative of the tissue and/or body fluids under investigation;
(b) testing said sample for the presence of amyloid protein with a humanized antibody according to the invention, or a chimeric antibody or a fragment thereof;
(c) determining the amount of humanized antibody bound to the protein; and
(d) calculating the plaque burden in the tissue and/or body fluids.

In particular, the invention relates to a method of determining the extent of amyloidogenic plaque burden in a tissue and/or body fluids, wherein the formation of the immunological complex in step c) is determined such that presence or absence of the immunological complex correlates with presence or absence of amyloid protein, in particular Aβ N3pE.

In still another embodiment, the invention relates to a composition comprising the humanized antibody according to the invention, or a chimeric antibody or a fragment thereof, and as described herein before including any functionally equivalent antibody or any derivative or functional parts thereof, in particular a composition which is a pharmaceutical composition optionally further comprising a pharmaceutically acceptable carrier.

In another embodiment of the invention, said composition comprises the humanized antibody in a therapeutically effective amount.

Further comprised by the invention is a mixture comprising a humanized antibody of the invention, or a chimeric antibody or a fragment thereof, and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the invention relates to a mixture, wherein the further biologically active substance is a compound used in the medication of amyloidosis, a group of diseases and disorders associated with amyloid or amyloid-like protein such as Aβ N3pE involved in neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

In another embodiment of the invention, the other biologically active substance or compound may also be a therapeutic agent that may be used in the treatment of amyloidosis caused by Aβ N3pE or may be used in the medication of other neurological disorders.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neuron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl- D-aspartate glutamate receptor antagonists, non-steroidal anti-inflammatory drugs, antioxidants, and serotonergic receptor antagonists.

More particularly, the invention relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3 APS), 1,3-propanedisulfonate (1,3PDS), α-secretase activators, β- and γ-secretase inhibitors, tau proteins, neurotransmitter, β-sheet breakers, attractants for amyloid beta clearing/depleting cellular components, inhibitors of N-terminal truncated amyloid beta including pyroglutamated amyloid beta 3-42, such as inhibitors of glutaminyl cyclase, anti-inflammatory molecules, or cholinesterase inhibitors (ChEIs) such as tacrine, rivastigmine, donepezil, and/or galantamine, MI agonists and other drugs including any amyloid or tau modifying drug and nutritive supplements, and nutritive supplements, together with an antibody according to the present invention and, optionally, a pharmaceutically acceptable carrier and/or a diluent and/or an excipient.

The invention further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the invention may comprise niacin or memantine together with an antibody according to the present invention and, optionally, a pharmaceutically acceptable carrier and/or a diluent and/or an excipient.

In a further embodiment, the mixtures according to the invention may comprise a glutaminyl cyclase inhibitor together with an antibody according to the present invention and, optionally, a pharmaceutically acceptable carrier and/or a diluent and/or an excipient.

Preferred inhibitors of glutaminyl cyclase are described in WO 2005/075436, WO 2008/055945, WO 2008/055947, WO 2008/055950, WO 2008/065141, WO 2008/110523, WO 2008/128981, WO 2008/128982, WO 2008/128983, WO 2008/128984, WO 2008/128985, WO 2008/128986, WO 2008/128987, WO 2010/026212, WO 2011/131748, WO 2011/029920, WO 2011/107530, WO 2011/110613, WO 2012/123563 and WO 2014/140279, the disclosure of which is incorporated herein by reference.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the invention, but particularly a chimeric antibody or a fragment thereof, or a humanized antibody or a fragment thereof according to the invention and as described herein and, optionally, a pharmaceutically acceptable carrier and/or a diluent and/or an excipient.

In a specific embodiment of the invention, the compositions and mixtures according to the invention and as described herein before comprise the humanized antibody of the invention and the biologically active substance, respectively, in a therapeutically effective amount.

Other compounds that can be suitably used in mixtures in combination with the humanized antibody according to the present invention are described in WO2008/065141 (see especially pages 37/38), including PEP-inhibitors (pp. 43/44), LiCI, inhibitors of dipeptidyl aminopeptidases, preferably inhibitors of DP IV or DP IV-like enzymes (see pp. 48/49); acetylcholinesterase (ACE) inhibitors (see p. 47), PIMT enhancers, inhibitors of beta secretases (see p. 41), inhibitors of gamma secretases (see pp. 41/42), inhibitors of neutral endopeptidase, inhibitors of phosphodiesterase-4 (PDE-4) (see pp. 42/43), TNFalpha inhibitors, muscarinic M1 receptor antagonists (see p. 46), NMDA receptor antagonists (see pp. 47/48), sigma-1 receptor inhibitors, histamine H3 antagonists (se p. 43), immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS; beta-amyloid antibodies (see p. 44), cysteine protease inhibitors (see p. 44); MCP-1 antagonists (see pp. 44/45), amyloid protein deposition inhibitors (see 42) and beta amyloid synthesis inhibitors (see p. 42), which document is incorporated herein by reference.

In another embodiment, the invention relates to a mixture comprising the humanized antibody according to the invention, or a chimeric antibody or a fragment thereof and as described herein before and/or the biologically active substance in a therapeutically effective amount.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 21th Edition, Gennaro, Ed., Mack Publishing Co., Easton, Pa., 2005.

The pharmaceutically acceptable carriers or diluents as well as any other known adjuvants and excipients should be suitable for the chosen humanized antibody of the present invention and the chosen mode of administration. Suitability for carriers and other components of pharmaceutical compositions is determined based on the lack of significant negative impact on the desired biological properties of the chosen humanized antibody or pharmaceutical composition of the present invention (e.g., less than a substantial impact (10% or less relative inhibition, 5% or less relative inhibition, etc.)) on antigen binding.

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular humanized antibody being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a humanized antibody of the present invention in vivo and in vitro are well known in the art and may be selected by those of ordinary skill in the art.

In one embodiment, a pharmaceutical composition of the present invention is administered parenterally.

The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a humanized antibody of the present invention.

Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active humanized antibody, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The humanized antibodies of the present invention may be prepared with carriers that will protect the humanized antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the antibodies of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the humanized antibody, use thereof in the pharmaceutical compositions of the present invention is contemplated.

Pharmaceutical compositions for injection must typically be sterile and stable under the conditions of manufacture and storage. The composition may be formulated as a solution, microemulsion, liposome, or other ordered structure suitable to high drug concentration. The carrier may be a aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the humanized antibody in the required amount in an appropriate solvent with one or a combination of ingredients e.g. as enumerated above, as required, followed by sterilization microfiltration. Generally, dispersions are prepared by incorporating the humanized antibody into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the humanized antibody in the required amount in an appropriate solvent with one or a combination of ingredients enumerated above, as required, followed by sterilization microfiltration. Generally, dispersions are prepared by incorporating the humanized antibody into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of humanized antibody calculated to produce the desired therapeutic effect in association with the required pharmaceutical carrier. The specification for the dosage unit forms of the present invention are dictated by and directly dependent on (a) the unique characteristics of the humanized antibody and the particular therapeutic effect to be achieved, and (b) the limitations inherent in the art of compounding such an humanized antibody for the treatment of sensitivity in individuals.

The effective dosages and the dosage regimens for the humanized antibodies of the invention depend on the disease or condition to be treated and may be determined by the persons skilled in the art. An exemplary, non-limiting range for a therapeutically effective amount of an antibody of the present invention is about 0.1-10 mg/kg/body weight, such as about 0.1-5 mg/kg/body weight, for example about 0.1-2 mg/kg/body weight, such as about 0.1-1 mg/kg/body weight, for instance about 0.15, about 0.2, about 0.5, about 1, about 1.5 or about 2 mg/kg/body weight.

A physician or veterinarian having ordinary skill in the art may readily determine and prescribe the effective amount of the pharmaceutical composition required. For example, the physician or veterinarian could start doses of the specified humanized antibody employed in the pharmaceutical composition at levels lower than that required in order to achieve the desired therapeutic effect and gradually increase the dosage until the desired effect is achieved. In general, a suitable daily dose of a composition of the present invention will be that amount of the humanized antibody which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a humanized antibody of the present invention to be administered alone, it is preferable to administer the humanized antibody as a pharmaceutical composition as described above.

Examples

1. Humanization Approach to Generate N3pE-Aβ Specific Humanized Antibodies

N3pE-Aβ specific mouse monoclonal antibody clones #6, #17 and #24 were obtained from hybridoma cell lines 6-1-6, 17-4-3, and 24-2-3, which have been deposited in accordance with the Budapest Treaty and are available at the Deutsche Sammlung für Mikroorganismen und Zellkulturen (DSMZ) in Braunschweig, Del., with a deposit date of Jun. 17, 2008, and with the respective deposit numbers (clone 6-1-6): DSM ACC2924
(clone 17-4-3): DSM ACC2925
(clone 24-2-3): DSM ACC2926.

The first step in humanization process of antibody clones #6, #17 and #24 was the definition of the CDRs in the variable domains of light and heavy chains. By Rosetta Antibody Modeling Server (http://antibody.graylab.jhu.edu) the CDRs were predicted. FIG. 1 shows exemplary the CDRs predicted for clone #6.

To select the appropriate framework for CDR-Grafting human sequences with the highest similarity to the non-human antibody need to be identified. By Blast analysis the variable domain of the light chain (Lv) and the heavy chain (Hv) were separately fitted with the pool of published human sequences. For the light chain a human antibody sequence with 82% identity was found, which belongs to the class of kappa LC. The highest homology for the heavy chain has a human amino acid sequence with 62% identity.

To group the selected human antibody framework sequence to germline gene sequences, a Blast search was performed in the germline libary IMGT. For light chain clone #6 and clone #24a sequence with the sequence code IGKV2-30*01 was found. The light chain variable region of clone #17 was most similar to IGKV2-30*02. The heavy chain variable region codes could be identified with IGHV1-3*01, IGHV1-69*13 and IGHV3-48*01 corresponding to clone #6, clone #17 and clone #24, respectively. Table 1 shows the framework parameters of variable regions of the humanized antibodies.

TABLE 1

Framework parameters of variable regions of the humanized antibodies.

| clone# | Lv | | | Hv | | |
|---|---|---|---|---|---|---|
| | Aa | acc nr. | family | aa | acc nr. | family |
| 6 | BAC01730.1 | AB064102.1 | IGKV2-30*01 | AAS85817.1 | AY392875.1. | IGHV1-3*01 |
| 24 | BAC01730.1 | AB064102.1 | IGKV2-30*01 | AAD30405.1 | AF115119.1 | IGHV1-69*13 |
| 17 | BAC01734.1 | AB064106.1 | 1GKV2-30*02 | AAS858165 | AY392925.1 | IGHV3-48*01 | aa = amino acid sequence, acc nr. = accession number, family = gene family

By CDR grafting the CDRs of the mouse antibody clones #6, #17 and #24 were combined with the respective human antibody framework to create a humanized antibody. The heavy chain constant region of human IgG1 was used for reconstitution the entire antibodies. The light chain variable domains were fused to the human kappa chain constant region.

2. RNA Isolation and cDNA Synthesis

As source for constant sequences, RNA of human B cells was isolated by lysis of 500 µl whole blood with 5 ml 1× FACS Lysis Solution (Becton Dickinson) for 10 minutes at room temperature. The lysate was centrifuged at 300 g for 5 min; the pellet was washed two times with PBS and was then resolved in 350 µl RA1 Buffer of Nucleo Spin® RNA II (Macherey-Nagel) and added with 3.5 µl 0.5M TCEP (SIGMA). The RNA was isolated by manufacturers' instructions. 10 µl of RNA was first incubated with 1 µl 0.5 µg/µl OligodT Primer (Invitrogen) and 1 µl 10 mM dNTPs for 5 min at 65° C. Then 4 µl of 5× First Strand Buffer (Invitrogen), 2 µl of 100 mM DTT and 0.5 µl SuperScript III Reverse Transcriptase (Invitrogen) was added to 20 µl and mix was incubated for 5 minutes at 25° C., 50 min at 50° C. and 15 min at 70° C. By PCR with primer pairs shown in Table 2, synthesized cDNA of constant region of light and heavy chain could be amplified.

TABLE 2

Primer for cloning of constant region

| SEQ ID NO | Name | Sequence |
|---|---|---|
| 44 | hkappa5' | ACTGTGGCTGCACCATCTGTCTTC |
| 45 | hkappa3' | CTAACACTCTCCCCTGTTGAAGCTC |
| 46 | hIgG1Hc5'1 | AGGGAACCCTGGTCACCGTCTCC |
| 47 | hIgG1Hc3' | TCATTTACCCGGAGACAGGGAGAGG |

For amplification of the PCR product of humanized light chain clone #6 following forward and reverse primers were used:

```
RT_chim_humKI6f:
                        (SEQ ID NO: 48)
CAAGTCAGAGCCTCTTATATAGTG;

RT_chim_humKI6r:
                        (SEQ ID NO: 49)
GTACCTTGCACGCAGTAATAAAC.
```

For amplification of the reference gene mouse HPRT Primer were used.

To perform the amplification 7.5 µl Sybergreen (Firma), 1 µl Primer forward (25 pmol/µl), 1 µl Primer reverse (25 pmol/µl), 5.5 µl ddH$_2$O and 1 µl cDNA were used in cycler.

3. Expression of Recombinant Antibody in CHO Cells by Separately Cloning LC and HC into Two Different Expression Plasmids The sequences of the light and heavy chain of the humanized antibodies were separately cloned into two different mammalian expression vectors, pCDNA3.1 and HC-pOptiVEC respectively. To identify the optimal combination of vectors to express the recombinant antibody in CHO cell culture, different plasmid combinations were used to perform transient expressions in adherent CHO cells. In a second step, it was investigated whether different DNA ratios between LC and HC plasmid influences the expression level. With transfection of 3 µg LC-pCDNA3.1 and 1 µg HC-pOptiVEC, an increased expression level was found.

For further adherent CHO cells expression of humanized antibody, plasmid combination of LC-pCDNA3.1 and 1 µg HC-pOptiVEC and a plasmid DNA ratio of LC 3:1 HC was used.

Freestyle™ CHO suspension cells were used in the following transfections to cultivate a higher amount of transient expressing cells which to generate recombinant antibodies. First was tested whether an excess of LC plasmid could improve the expression of antibody like in case of the adherent cells. Like in adherent CHO cells a LC to HC plasmid DNA ratio of 1:1 and 3.1 was used. Western blot analysis revealed that an excess of LC plasmid increases the expression of humanized antibody as in the case of adherent CHO cells. By measurement of cell viability it become obvious, that the cell viability decreases to about 50% of transfected cells after 6 days. After day six, no further increase of antibody level in supernatant was detectable. Consequently, culture supernatants were harvest at day six in the case of following transfections.

To investigate if the produced antibodies are efficient transported into the cell supernatant, a cell lysate sample was applied to SDS PAGE, analyzed by Western blot. GAPDH, a housekeeping cytoplasmic protein was used for reference loading comparable amounts of cell lysate protein to the SDS gel. In cell lysate of humanized antibody expressing CHO cells a strong band of 120 kDa occurs migrating at the same size as detected in the cell supernatant.

4. Purification of Recombinant Antibody by Protein G Chromatography

Figure 2:
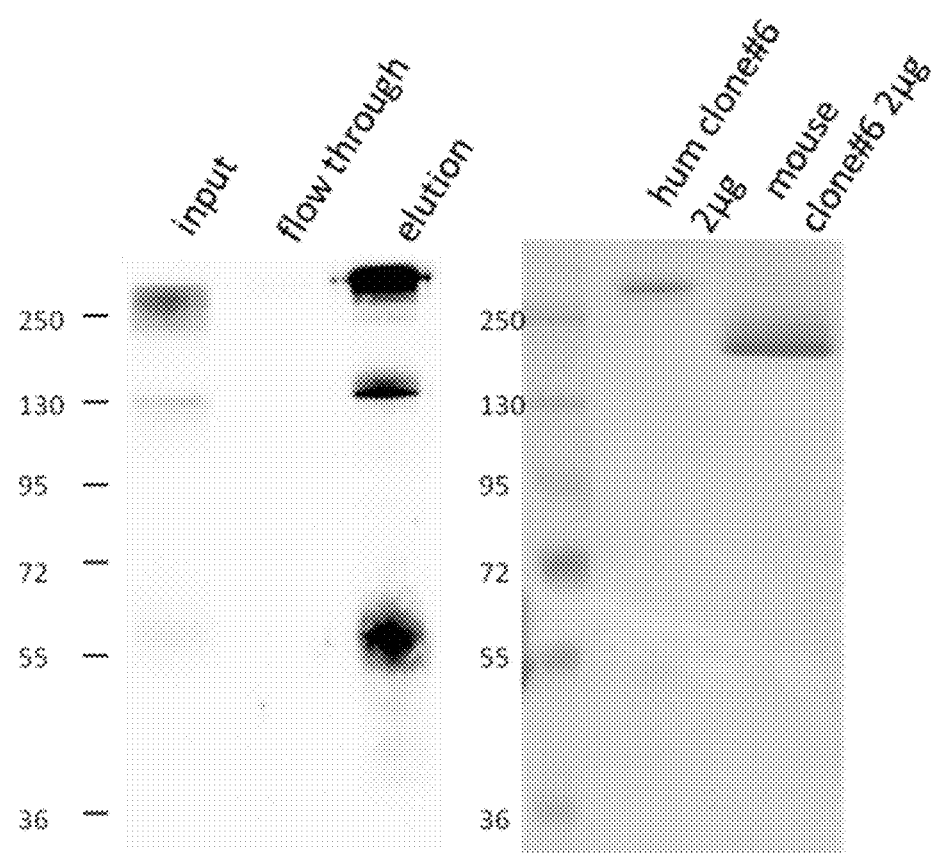
FIG. 2 shows the purification of humanized antibody clone #6 by Protein G chromatography. Recombinant produced humanized antibody clone #6 was purified by Protein G Chromatography. 24 µl of input fraction (lane 1), flow through fraction (lane 22) and elution fraction (lane 3) are loaded onto 10% SDS PAGE under non reducing conditions. 2 µg of and humanized (lane 4) antibody were compared to mouse antibody (lane 5) in 10% coomassie stained SDS gel.

The humanized antibody clone #6 was purified to investigate the antigen binding property of the protein in comparison with the original murine antibody. Therefore 300 ml supernatant with expressed chimeric and humanized antibody was produced and purified by Protein G chromatography (FIG. 2). Because the amount of expressed antibody was very low, the yield was less than 0.1 µg/ml, in total 25 µg purified protein. The eluted antibody was concentrated to about 200 µg/ml and 2 µg protein was applied to SDS-PAGE following coomassie staining (FIG. 2).

Figure 3:
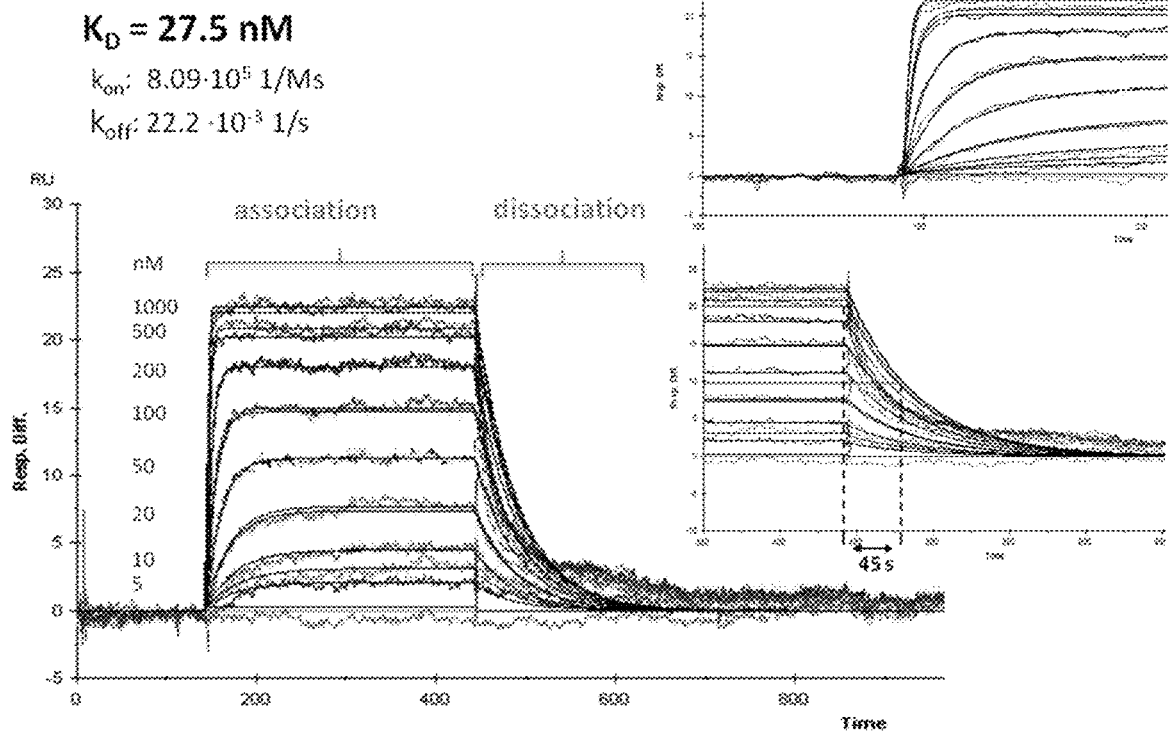
FIG. 3 shows the calculation of KD of humanized antibody clone #6 HC T97 variant and LC L41 variant. The binding affinities of HC T97 and LC L41 variant of humanized antibody clone #6 to Aβ(pE3-18) was measured by SPR using peptide concentrations of 1-100 nM (HC T97 variant) and 10-1000 nM (LC L41 variant). The KD is calculated with 5.3 nM. The KD value of LC L41 variant was determined with 162.7 nM by plotting $RU_{equ}$ values against the peptide concentration and fitting by steady-state model as described above
Figure 3:
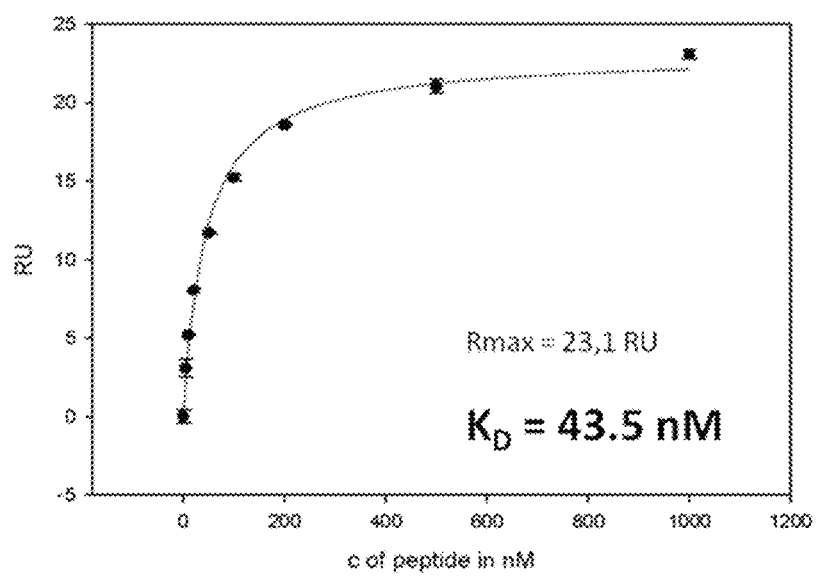

5. Surface Plasmon Resonance Measurement to Compare Antigen Binding of Murine and Humanized Antibody Surface Plasmon Resonance measurement was used to investigate the binding efficacy of humanized antibody to AβpE3-18 (FIG. 3). To prevent mass transfer and avidity effects during measurement, the following procedure was used.

First a polyclonal α-human antibody was coupled to an SPR-Chip subsequent loaded with the humanized antibody until the Response Unit was more than 1000.

Kinetic measurement was performed at different concentrations (of 5 to 1000 nM) of AβpE3-18-peptide. The graphs of the measured series are shown as an overlay plot with the sensorgrams, corrected by the sensogram measuring the running buffer, aligned at the time of injection and the baseline adjusted to zero before injection. The results are evaluated according to a simple 1:1 interaction model (Langmuir fit), which promote the $k_{off}$ and $k_{on}$ rate constants. In FIG. 3 the SPR-binding curves are shown, consisting of association and dissociation curve.

Apparent kinetic constants according to the 1:1 Langmuir fitting are listed in Table 3. Due to the fact that the humanized antibody is non-covalently bound to the chip surface, small amounts of antibody molecules were washed out during the measurement. Therefore the Rmax values were fitted locally for every single sensogramm.

TABLE 3

Statistics of Langmuir fit in kinetics of humanized antibody clone#6

| Aβ$_{pE3-18}$ in nM | $k_{on}$ (1/Ms) | $k_{off}$ (1/s) | Rmax (RU) | RI (RU) | KA (1/M) | KD (M) | Req (RU) | Chi2 |
|---|---|---|---|---|---|---|---|---|
|  | 8.09E+05 | 0.0222 |  | 0.303 | 3.65E+07 | 2.74E−08 | 0.803 |  |
| 0 |  |  | 1.19 |  |  |  | 0 | 1.measurement |
| 5 |  |  | 18.1 |  |  |  | 2.79 |  |
| 10 |  |  | 15.5 |  |  |  | 4.15 |  |

TABLE 3-continued

Statistics of Langmuir fit in kinetics of humanized antibody clone#6

| $A\beta_{pE3-18}$ in nM | $k_{on}$ (1/Ms) | $k_{off}$ (1/s) | Rmax (RU) | RI (RU) | KA (1/M) | KD (M) | Req (RU) | Chi2 |
|---|---|---|---|---|---|---|---|---|
| 20 | | | 16.7 | | | | 7.05 | |
| 50 | | | 16.9 | | | | 10.9 | |
| 100 | | | 18.7 | | | | 14.7 | |
| 200 | | | 20.2 | | | | 17.7 | |
| 500 | | | 21.7 | | | | 20.5 | |
| 1000 | | | 22.7 | | | | 22.1 | |
| 0 | | | 0 | | | | 0 | 2.measurement |
| 5 | | | 11.4 | | | | 1.76 | |
| 10 | | | 15.5 | | | | 4.14 | |
| 20 | | | 17.5 | | | | 7.39 | |
| 50 | | | 16.9 | | | | 10.9 | |
| 100 | | | 18.3 | | | | 14.4 | |
| 200 | | | 20.2 | | | | 17.7 | |
| 500 | | | 21 | | | | 19.9 | |
| 1000 | | | 22.3 | | | | 21.7 | |

The plot of the curves during association of peptide (FIG. 3A, upper inset) fits very well, whereas the plot of peptide dissociation curves (FIG. 3A, lower inset) don't localize accurate on experimental curves. With the fit the kinetic parameter $k_{off}$ of 22.2 $10^{-3}$ 1/s was computed (Table 2). This parameter describes the time which is necessary for removing the half of bounded peptide. This means that during 1/0,0222 s=45 s the half of injected peptide is removed (see FIG. 3A, lower inset). Because Langmuir fit doesn't match very well during dissociation phase, $K_D$ determination was performed by fitting $R_{equ}$ values over peptide concentration (FIG. 3B) using following equation: $R_{equ} = R_{max} \cdot K_A \cdot c/(1 + K_A \cdot c)$, at which $R_{equ}$ the signal in equilibrium with corresponding concentration c are variables and $R_{max}$ and $K_A$ the constants to fit. $K_D$ can be calculated by $1/K_A$.

By structural analysis of mouse Fab fragment antibody clone #6 was concluded that Thr97 in HC could have an important effect on binding affinity to AβpE3. After replacement of Ala97 by Thr97 in the humanized antibody clone #6 an improved binding affinity was yielded with nearly the same KD value compared to the mouse antibody clone #6. Higher amount of expressed antibody was required to prove these findings by additional ITC measurement. Therefore the expression level was increased by a replacement of LC and HC signal sequences of humanized antibody T97 variant by the murine sequences. In a second step generation of a stable cell line was performed to increase antibody production.

Table 4 shows the apparent kinetic constants according to the 1:1 Langmuir fitting of further sequence variants of humanized antibody clone #6:

| Variant | $K_D$ (nM) | kon ($s^{-1}M^{-1}$) | koff ($s^{-1}$) |
|---|---|---|---|
| VH: SEQ ID NO: 24<br>VL: SEQ ID NO: 14 | 9.36 | $6.16 \times 10^5$ | $5.76 \times 10^{-3}$ |
| VH: SEQ ID NO: 27<br>VL: SEQ ID NO: 14 | 5.09 | $6.35 \times 10^5$ | $3.23 \times 10^{-3}$ |
| VH: SEQ ID NO: 27<br>VL: SEQ ID NO: 15 | 15.5 | $2.67 \times 10^5$ | $4.15 \times 10^{-3}$ |
| VH: SEQ ID NO: 27<br>VL: SEQ ID NO: 13 | 7.35 | $5.62 \times 10^5$ | $4.13 \times 10^{-3}$ |
| VH: SEQ ID NO: 70<br>VL: SEQ ID NO: 14 | 8.43 | $4.23 \times 10^5$ | $3.57 \times 10^{-3}$ |

6. Stable Cell Line Generation of Humanized Antibody Variant HC T97 For stable cell line development first a pool of stable CHO-DG44 cell lines were generated by treatment with different concentrations of methotrexate (MTX). The best expression was detected accompanied by a low amount of dying cells at a concentration of 0.5 μM MTX (FIG. 14A, lane2). Thus, cells with pretreatment of 0.5 μM MTX were used for clonal selection by limiting dilution.

Figure 4:
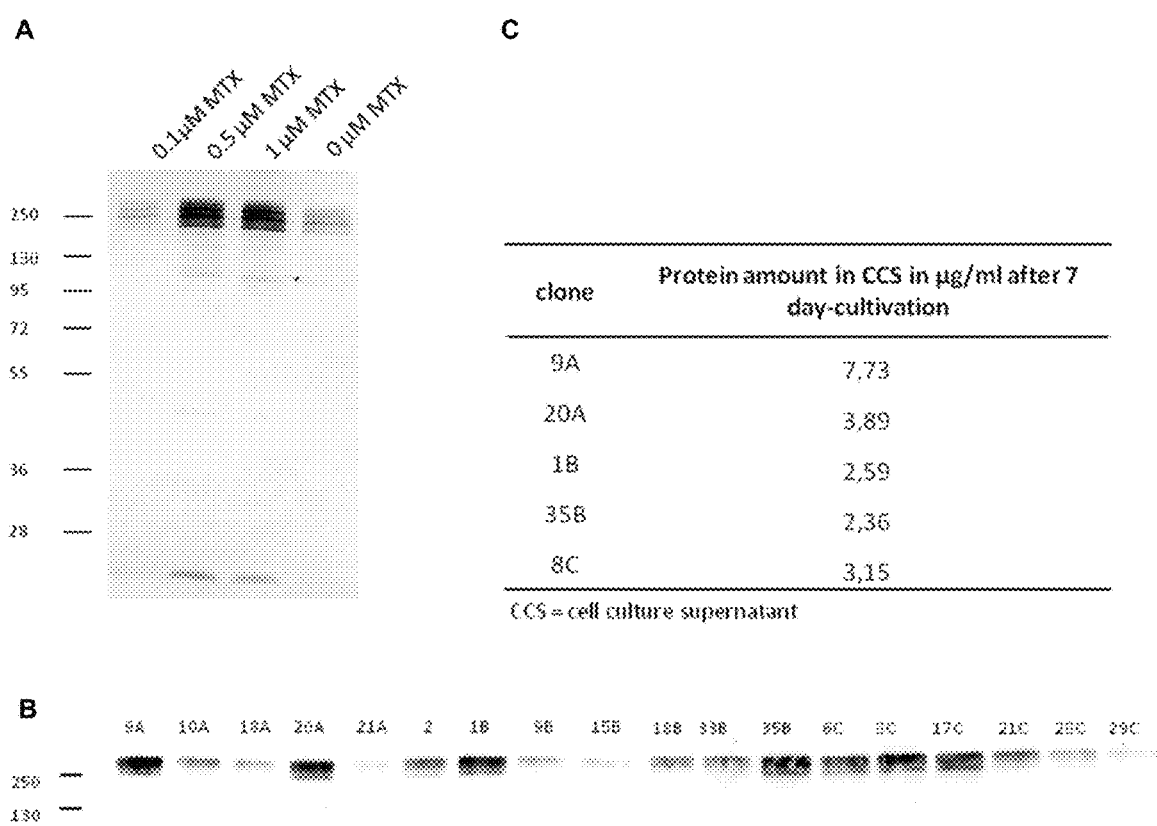
FIG. 4 shows the generation of stable cell line expressing humanized antibody clone #6 variant HC T97. A) MTX Treatment of CHO DG44 cells stable expressing humanized antibody clone #6 variant HC T97. 0.5 µM MTX (lane 2) leads to increasing expression in comparison with 0.1 µM and without MTX (lane 1 and 4). More over low amount of cells dying copared with treatment using 1 µM MTX (lane 4). 24 µl supernatant were loaded onto a 10% SDS PAGE under non reducing conditions. B) 18 clones were yielded after clonal selection by limiting dilution and analyzed by Western blot. 24 µl of supernatant were loaded onto a 12% SDS PAGE under non reducing conditions. C) Five of these 18 clones were scaled up and cultivated for 7 days, so expression levels in supernatant could be analyzed by SPR.

One hundred potential antibody expressing clones were found after clonal selection. The supernatant of these clones were diluted 1:20 in HBS-EP buffer and analyzed by SPR using an AβpE3-18 coupled chip. A calibration curve was used to determine the antibody concentration in supernatant. 18 clones were separated which show a started antibody concentration over 0.15 μg/ml after 3 days of expression. These clones were scaled up in 24 well format and supernatants were collected and analyzed by Western blot (FIG. 4B). Five of these clones revealed good expression and were further scaled up until 30 ml shaking culture. After 7 day expression time the expression level was measured by SPR (FIG. 4C). Clone 9A has shown the highest antibody concentration after 7 day cultivation. Therefore this clone was used for expression higher amounts of supernatant. The cultivation was performed without further selection pressure to get higher cell viability. Three liters of antibody containing supernatant were collected.

7. Purification of Humanized Antibody Clone #6 by Protein G Chromatography

One liter of supernatant was diluted with one liter 40 mM $Na_2HPO_4$ pH 7 and applied overnight to 5 ml Protein G column at 4° C. After that column was washed with binding buffer (20 mM $Na_2HPO_4$, pH 7, fraction A1-A3) and then with high-salt buffer (2 M NaCl, 40 mM $Na_2HPO_4$ pH 7, fraction A4-A7) to remove unspecific bound proteins. The antibody was eluted with 0.1M Glycin-HCl, pH 2.7 from column and immediately neutralized by 1 M Tris pH 9. Fractions were collected and 24 μl were loaded onto 12% SDS PAGE, respectively. The fractions A12+B1 were pooled and used for KD determination by ITC. Overall, 2.5 mg antibody was purified from one liter culture supernatant.

8. ITC Measurement of Humanized Antibody Clone #6 with AβpE3-18

Figure 5:
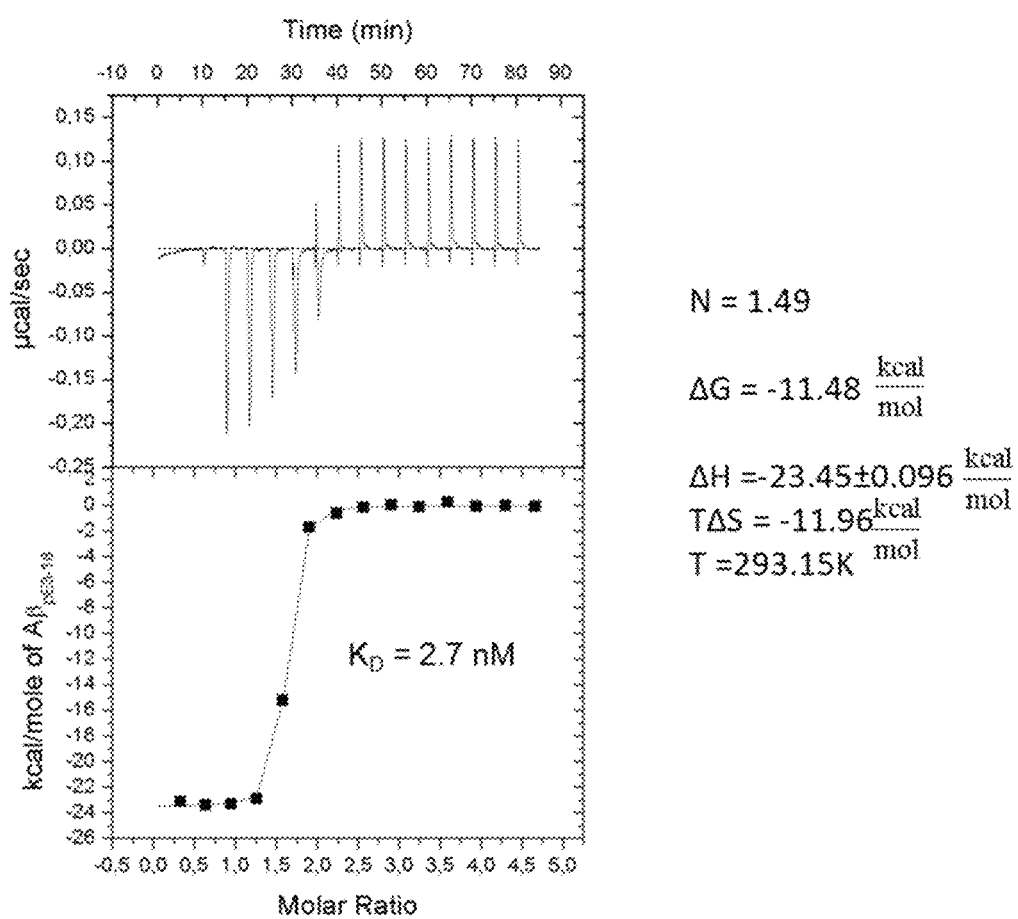
FIG. 5 shows the ITC measurement of humanized antibody clone #6 with AβpE3-18 peptide. Purified humanized antibody clone #6 HC T97 variant was used for ITC measurement. Top: raw data of ITC measurement. Bottom.

For determination of the $K_D$-Value, the humanized antibody clone #6 was diluted to a concentration of 1 μM. The ligand AβpE3-18 with a concentration of 20 μM was titrated at 293.15K. After integration of the raw data of ITC-measurement (FIG. 5B, bottom) the stoichiometry of 1.5 was calculated. The calculated $K_D$-Value was 2.7 nM according quite well with value of 5.3 nM calculated from the SPR data characterizing the humanized clone #6 HC T97 ligand binding in solvent as a high affine interaction. The interaction is driven mainly by enthalpic contributions (ΔH=−23.45 kcal/mol) and opposed by entropic penalties (TΔS=−11.96 kcal/mol), which is typical for structural rearrangement at the binding site by formation of hydrogen bonds yielding in significant loss of degrees of freedom.

9. Humanization, Expression and Purification of the Two Further AβpE3-Secific Antibodies Clone #17 and Clone #24

The humanization, expression and purification of the two further AβpE3-secific antibodies clone #17 and clone #24 was performed using the same protocols, materials and methods as well as experimental conditions as used for clone #6.

10. SPR Measurement with Humanized Antibody Clone #24 and Clone #17

SPR measurements using the pE3-Aβ18 ligand revealed that both humanized antibodies are capable to bind the pE3-Aβ peptide. The rate constants and the $K_D$ value could be calculated very well by Langmuir 1:1 model fit. The origin KD values of mouse antibodies to pE3-Aβ are shown in table 5. It became obvious that the $k_{off}$ value of humanized antibody clone #24 is 20 fold higher than the $k_{off}$ value of mouse antibody clone #24. This means that after humanization the pE3-Aβ peptide dissociates faster from the antigen binding pocket of the antibody.

different concentrations for one hour followed by washing. Receptor-bound H6 or H67 was detected with fluorochrome conjugated-anti-Fab'. Binding capacity was measured by FACS and the Kd and Bmax were calculated by non-linear regression.

Results: Both antibodies showed comparable binding to all receptors. See FIGS. 6, 7, 8 and 9.

12. Binding to C1q

The binding of two antibodies, which either comprised the human IgG1 Fc wild-type region of SEQ ID NO: 73 or the K324A mutant variant thereof (SEQ ID NO: 74), to C1q was compared in order to better characterize the effector functions of the antibodies.

A number of assay formats of binding of the antibodies to C1q was tested, including a) direct binding of the two antibodies to the plate and then biding to C1q in solution; and b) streptavidin coated plates first incubated with biotinylated pE-Aβ peptide, binding to antibodies and then C1q.

In summary, format a) produced best results. The procedure is summarized below:

The ELISA plate was coated with the antibody, comprising the human IgG1 Fc wild-type region of SEQ ID NO: 73, the K324A mutant variant thereof (SEQ ID NO: 74), and a K324A control (hu14.18K324A) that does not bind C1q at 10, 8, 6, 4, 3, 2, 1 and 0 μg/ml in triplicate and incubated at 4° C. overnight. Next day, the plate was washed three times with 1× PBS and then blocked with 1% BSA in 1× PBS at 50 μl/well. C1q (Sigma, Cat. #C1740) was added to each

TABLE 5

Determination of $k_{on}$, $k_{off}$ and $K_D$ value of different Aβ peptides

| Abeta | sequence | Ab clone# | KD in nM | $k_{on}$ in 1/Ms | $k_{off}$ in 1/s |
|---|---|---|---|---|---|
| human pE3-18 | pEFRHDSGYEVHHQKLV (SEQ ID NO: 50) | mouse 6 | 6.7 | 6.89E + 05 | 4.58E − 03 |
| | | mouse 24 | 2.2 | 1.76E + 05 | 0.38E − 03 |
| | | mouse 17 | 1.8 | 19.5E + 05 | 3.46E − 03 |
| | | human 6 | 5.3 | 6.89E + 05 | 4.58E − 03 |
| | | human 24 | 16 | 4.91E + 05 | 7.84E − 03 |
| | | human 17 | 1.5 | 19.9E + 05 | 2.90E − 03 |
| human 1-18 | DAEFRHDSGYEVHHQKLV (SEQ ID NO: 51) | mouse 6 | — | — | — |
| | | mouse 24 | — | — | — |
| | | mouse 17 | — | — | — |
| | | human 6 | — | — | — |
| | | human 17 | — | — | — |
| human 2-18 | AEFRHDSGYEVHHQKLV (SEQ ID NO: 52) | mouse 6 | n.d. | — | — |
| | | mouse 24 | n.d. | — | — |
| | | mouse 17 | 490 | 0.0741E + 05 | 3.63E − 03 |
| | | human 6 | n.d. | — | — |
| | | human 17 | 190 | 0.149E + 05 | 2.84E − 03 |
| human 4-18 | FRHDSGYEVHHQKLV (SEQ ID NO: 53) | mouse 6 | — | — | — |
| | | mouse 24 | — | — | — |
| | | mouse 17 | — | — | — |
| | | human 6 | — | — | — |
| | | human 17 | — | — | — |

11. Binding to Fc Gamma Receptors

The binding of two antibodies, which either comprised the human IgG1 Fc wild-type region of SEQ ID NO: 73 or the K324A mutant variant thereof (SEQ ID NO: 74), to different Fc gamma receptors (CD16A, CD32A, CD32B, and CD64) was compared.

The K324A mutant was produced by site-directed mutagenesis. The binding was measured in a FACS based bioassay to Chinese Hamster Ovary (CHO) cells stably expressing full length human CD16A, CD32A, CD32B, or CD64. Both antibodies were incubated with each cell line at 7 well at 2 μg/ml in blocking buffer and incubated for 1 hour at room temperature. The plate was then washed three times with 200 μl of 1× PBS. Anti-C1q-HRP (Thermo, Cat. #PA1-84324) was added to the plate to detect the binding at a 1:250 dilution in blocking buffer (50 μl/well) for 1 hour. The plate was washed again three times with 200 μl of 1× PBS. 50 μl of TMB (Invitrogen, Cat. #002023) was added to each well to visualize the interaction (Invitrogen, Cat. #002023) for 2 min. 50 μl of stop solution ((1M Sulfuric Acid) was added to each well before reading the absorbance at 450 nm.

Results: The antibody, which comprised the human IgG1 Fc wild-type region of SEQ ID NO: 73 did bind to C1q. The K324A mutant variant thereof (comprising the IgG1 Fc region of SEQ ID NO: 74), did not bind to C1q. See also FIG. 10.

13. Immunohistochemistry

With IHC the antigen Aβ N3pE can be localized in cerebral tissue sections. Therefore the humanized antibodies of the invention were used for detection of Aβ N3pE.

For the IHC human cerebral tissue sections of the hippocampus and the frontal cortex from AD patients and furthermore cerebral tissue sections of hippocampus from existing animal models for Alzheimer's disease as described herein can be used. These mouse models show increased brain Aβ levels followed by development of neuritic plaques. The tissue sections were paraffin-embedded and serial cut. The sections were stained with hematoxylin to colored nuclei of cells and then immunostained with the anti Aβ N3pE antibodies of the invention. The tissue section preparation and staining were performed in accordance with standard methodology.

14. Treatment of Alzheimer Mice In Vivo

A total of 62 male mice were utilized in this study. Prior to the start of immunization, four mice of an existing mouse model for Alzheimer's disease (avg. 5.6 mo±0.45) mice were sacrificed as baseline controls to assess cerebral Aβ plaque burden at the commencement of treatment. The remaining mice were divided into four groups and received the following treatment: 250 μl sterile PBS (n=12; avg. 5.89 mo±0.13), 200 μg of a humanized antibody of the invention. A group of age- and gender-matched Wt littermates were injected with 250 μl PBS (n=12; avg. 5.80 mo±0.12) and served as behavioral controls. Mice were treated with a total volume of 250 μl (antibody or PBS) via intraperitoneal injection for 28 weeks.

Euthanasia and Tissue Preparation

Mice were euthanized, perfused and plasma harvested at 6 months (baseline) or 13 months of age. The brain was extracted and divided sagittally. The hippocampus, cortex and cerebellum were dissected from one hemisphere and snap frozen for biochemical analyses.

The other hemisphere was drop-fixed in 4% parafomaldehyde (Electron Microscopy Sciences) for 24 h at 4° C., cryoprotected in graded sucrose solutions at 4° C. and embedded in OCT compound (Tissue Tek).

---

The invention claimed is:

1. A humanized antibody or a functional variant thereof, wherein the variable part of the light chain of said antibody comprises an amino acid sequence selected from the group consisting of SEQ ID NO: 7, SEQ ID NO: 11, SEQ ID NO: 13 and SEQ ID NO: 14 comprising the CDR regions $V_L$ CDR1 of SEQ ID NO: 12, $V_L$ CDR2 SEQ ID NO: 9 and $V_L$ CDR3 of SEQ ID NO: 10 in the light chain; and wherein the variable part of the heavy chain of said antibody comprises the CDR regions $V_H$ CDR1: SEQ ID NO: 25, $V_H$ CDR2: SEQ ID NO: 71; and $V_H$ CDR3: SEQ ID NO: 20.

2. The humanized antibody of claim 1, wherein the variable part of the light chain comprises the amino acid sequence of SEQ ID NO: 11.

3. The humanized antibody of claim 1, wherein the variable part of the light chain comprises the amino acid sequence of SEQ ID NO: 13.

4. The humanized antibody of claim 1, wherein the variable part of the light chain comprises the amino acid sequence of SEQ ID NO: 14.

5. The humanized antibody of claim 1, wherein the variable part of the heavy chain comprises the amino acid sequence of SEQ ID NO: 24.

6. The humanized antibody of claim 5, comprising the CDR regions:
$V_H$ CDR1: SEQ ID NO: 25, $V_H$ CDR2: SEQ ID NO: 71;
$V_H$ CDR3: SEQ ID NO: 20 in the heavy chain.

7. The humanized antibody of claim 1, wherein the variable part of the heavy chain comprises the amino acid sequence of SEQ ID NO: 70.

8. The humanized antibody of claim 7, comprising the CDR regions:
$V_H$ CDR1: SEQ ID NO: 25, $V_H$ CDR2: SEQ ID NO: 71;
$V_H$ CDR3: SEQ ID NO: 20 in the heavy chain.

9. The humanized antibody according to claim 1, having a human IgG1 Fc region which comprises an amino acid sequence selected from the group consisting of SEQ ID NO: 73 and SEQ ID NO: 74.

10. The humanized antibody according to claim 1, having a human IgG1 Fc region which comprises the amino acid sequence of SEQ ID NO: 74.

11. The humanized antibody according to claim 1, wherein the variable part of the light chain comprises the amino acid sequence of SEQ ID NO: 14; and having a variable part of a heavy chain which comprises the amino acid sequence of SEQ ID NO: 70; and having a human IgG1 Fc region which comprises the amino acid sequence of SEQ ID NO: 74.

12. The humanized antibody according to claim 1, having a variable part of a light chain, a variable part of a heavy chain, and a human IgG1 Fc region, wherein:
 the variable part of the light chain comprises the amino acid sequence of SEQ ID NO: 14; and
 the variable part of the heavy chain comprises the amino acid sequence of SEQ ID NO: 70; and
 the human IgG1 Fc region comprises the amino acid sequence of SEQ ID NO: 74;
 the variable part of the light chain comprises the CDR regions $V_L$ CDR1 of SEQ ID NO: 12, $V_L$ CDR2 of SEQ ID NO: 9 and $V_L$ CDR3 of SEQ ID NO: 10; and the variable part of the heavy chain comprises the CDR regions $V_H$ CDR1 of SEQ ID NO: 25, $V_H$ CDR2 of SEQ ID NO: 71 and $V_H$ CDR3 of SEQ ID NO: 20.

13. A pharmaceutical composition comprising the humanized antibody according to claim 1.

14. The pharmaceutical composition of claim 13, further comprising a further biologically active substance and/or a pharmaceutically acceptable carrier and/or a diluent and/or an excipient.

15. The pharmaceutical composition of claim 14, wherein said further biologically active substance is selected from a neuron-transmission enhancer, psychotherapeutic drug, an acetylcholine esterase inhibitor, a calcium-channel blocker, a biogenic amine, a benzodiazepine tranquillizer, an acetylcholine synthesis, storage or release enhancer, an acetylcholine postsynaptic receptor agonist, a monoamine oxidase-A or -B inhibitor, a N-methyl- D-aspartate glutamate receptor antagonist, a non-steroidal anti-inflammatory drug, an antioxidant, and a serotonergic receptor antagonist.

16. The pharmaceutical composition of claim 14, wherein said further biologically active substance is selected from the group consisting of a compound effective against oxidative stress, an anti-apoptotic compound, a metal chelator, an inhibitor of DNA repair, an α-secretase activator, a β- and γ-secretase inhibitor, a tau protein, a neurotransmitter, a β-sheet breaker, an anti-inflammatory molecule, a cholinesterase inhibitor, a MI agonist, a amyloid- or tau-burden modifying drug, a nutritive supplement, memantine, and a glutaminyl cyclase inhibitor.

17. The pharmaceutical composition of claim 15 wherein the further biologically active substance is acetylcholine esterase inhibitor.

18. The pharmaceutical composition of claim 16 wherein the further biologically active substance is a glutaminyl cyclase inhibitor.

* * * * *

SEQUENCE LISTING

```
<160> NUMBER OF SEQ ID NOS: 74

<210> SEQ ID NO 1
<211> LENGTH: 42
<212> TYPE: PRT
<213> ORGANISM: Human

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Human

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 38
<212> TYPE: PRT
<213> ORGANISM: Human

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

Gly Leu Met Val Gly Gly
        35

<210> SEQ ID NO 4
<211> LENGTH: 40
<212> TYPE: PRT
<213> ORGANISM: Human

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 5
<211> LENGTH: 38
<212> TYPE: PRT
<213> ORGANISM: Human

<400> SEQUENCE: 5

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 6
<211> LENGTH: 36
<212> TYPE: PRT
<213> ORGANISM: Human

<400> SEQUENCE: 6

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly
        35

<210> SEQ ID NO 7
<211> LENGTH: 112
<212> TYPE: PRT
<213> ORGANISM: Artificial sequence
<220> FEATURE:
<223> OTHER INFORMATION: variable part of light chain
<220> FEATURE:
<221> NAME/KEY: VARIANT
<222> LOCATION: (31)..(31)
<223> OTHER INFORMATION: Xaa is His or Tyr
<220> FEATURE:
<221> NAME/KEY: VARIANT
<222> LOCATION: (53)..(53)
<223> OTHER INFORMATION: Xaa is Ala, Ile or Thr

<400> SEQUENCE: 7

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Xaa Ser
            20                  25                  30

Asp Gly Lys Thr Tyr Leu Asn Trp Phe Gln Gln Arg Pro Gly Gln Ser

```
                35                  40                  45
Pro Arg Arg Leu Xaa Tyr Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95

Thr His Phe Pro Phe Thr Phe Gly Gly Gly Thr Lys Val Glu Ile Lys
            100                 105                 110

<210> SEQ ID NO 8
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: Variant
<222> LOCATION: (8)..(8)
<223> OTHER INFORMATION: Xaa is His or Tyr

<400> SEQUENCE: 8

Lys Ser Ser Gln Ser Leu Leu Xaa Ser Asp Gly Lys Thr Tyr Leu Asn
 1               5                  10                  15

<210> SEQ ID NO 9
<211> LENGTH: 7
<212> TYPE: PRT
<213> ORGANISM: Homo sapiens

<400> SEQUENCE: 9

Leu Val Ser Lys Leu Asp Ser
 1               5

<210> SEQ ID NO 10
<211> LENGTH: 7
<212> TYPE: PRT
<213> ORGANISM: Homo sapiens

<400> SEQUENCE: 10

Val Gln Gly Thr His Phe Pro
 1               5

<210> SEQ ID NO 11
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 11

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Tyr Ser
             20                  25                  30

Asp Gly Lys Thr Tyr Leu Asn Trp Phe Gln Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Val Gln Gly
                 85                  90                  95
```

```
                    85                  90                  95

Thr His Phe Pro Phe Thr Phe Gly Gly Gly Thr Lys Val Glu Ile Lys
                100                 105                 110

<210> SEQ ID NO 12
<211> LENGTH: 16
<212> TYPE: PRT
<213> ORGANISM: Artificial sequence
<220> FEATURE:
<223> OTHER INFORMATION: Synthetic peptide

<400> SEQUENCE: 12

Lys Ser Ser Gln Ser Leu Leu Tyr Ser Asp Gly Lys Thr Tyr Leu Asn
1               5                   10                  15

<210> SEQ ID NO 13
<211> LENGTH: 112
<212> TYPE: PRT
<213> ORGANISM: Artificial Sequence
<220> FEATURE:
<223> OTHER INFORMATION: Synthetic peptide

<400> SEQUENCE: 13

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Phe Gln Gln Arg Pro Gly Gln Ser
        35                  40                  45

Pro Arg Arg Leu Ala Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Phe Thr Phe Gly Gly Gly Thr Lys Val Glu Ile Lys
                100                 105                 110

<210> SEQ ID NO 14
<211> LENGTH: 112
<212> TYPE: PRT
<213> ORGANISM: Artificial
<220> FEATURE:
<223> OTHER INFORMATION: Synthetic peptide

<400> SEQUENCE: 14

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Phe Gln Gln Arg Pro Gly Gln Ser
        35                  40                  45

Pro Arg Arg Leu Thr Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Phe Thr Phe Gly Gly Gly Thr Lys Val Glu Ile Lys
                100                 105                 110
```

<210> SEQ ID NO 15
<211> LENGTH: 112
<212> TYPE: PRT
<213> ORGANISM: Artificial
<220> FEATURE:
<223> OTHER INFORMATION: Synthetic peptide

<400> SEQUENCE: 15

```
Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Phe Gln Gln Arg Pro Gly Gln Ser
        35                  40                  45

Pro Arg Arg Leu Thr Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Phe Thr Phe Gly Gly Gly Thr Lys Val Glu Ile Lys
            100                 105                 110
```

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

```
Lys Ser Ser Gln Ser Leu Leu His Ser Asp Gly Lys Thr Tyr Leu Asn
1               5                   10                  15
```

<210> SEQ ID NO 17
<211> LENGTH: 119
<212> TYPE: PRT
<213> ORGANISM: artificial sequence
<220> FEATURE:
<223> OTHER INFORMATION: Synthetic peptide
<220> FEATURE:
<221> NAME/KEY: Variant
<222> LOCATION: (32)..(32)
<223> OTHER INFORMATION: Xaa is His or Tyr
<220> FEATURE:
<221> NAME/KEY: Variant
<222> LOCATION: (54)..(54)
<223> OTHER INFORMATION: Xaa is Ser or Tyr
<220> FEATURE:
<221> NAME/KEY: Variant
<222> LOCATION: (56)..(56)
<223> OTHER INFORMATION: Xaa is Gly, Thr, Ala or Glu
<220> FEATURE:
<221> NAME/KEY: Variant
<222> LOCATION: (65)..(65)
<223> OTHER INFORMATION: Xaa is Lys or Gln
<220> FEATURE:
<221> NAME/KEY: Variant
<222> LOCATION: (70)..(70)
<223> OTHER INFORMATION: Xaa is Leu or Ile
<220> FEATURE:
<221> NAME/KEY: Variant
<222> LOCATION: (71)..(71)
<223> OTHER INFORMATION: Xaa is Ile or Thr
<220> FEATURE:
<221> NAME/KEY: Variant
<222> LOCATION: (80)..(80)

<223> OTHER INFORMATION: Xaa is Tyr or His
<220> FEATURE:
<221> NAME/KEY: Variant
<222> LOCATION: (93)..(93)
<223> OTHER INFORMATION: Xaa is Val or Thr

<400> SEQUENCE: 17

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly Xaa
            20                  25                  30

Thr Met Asn Trp Val Arg Gln Ala Pro Gly Gln Gly Leu Glu Trp Met
        35                  40                  45

Gly Leu Ile Asn Pro Xaa Asn Xaa Val Thr Arg Tyr Asn Gln Lys Phe
50                  55                  60

Xaa Gly Arg Val Thr Xaa Xaa Arg Asp Thr Ser Thr Thr Thr Val Xaa
65                  70                  75                  80

Met Glu Leu Thr Ser Leu Thr Ser Glu Asp Thr Ala Xaa Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser
        115

<210> SEQ ID NO 18
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: Variant
<222> LOCATION: (7)..(7)
<223> OTHER INFORMATION: Xaa is Tyr or His

<400> SEQUENCE: 18

Gly Tyr Ser Phe Thr Gly Xaa Thr Met Asn
1               5                   10

<210> SEQ ID NO 19
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: Variant
<222> LOCATION: (5)..(5)
<223> OTHER INFORMATION: Xaa is Tyr or Ser
<220> FEATURE:
<221> NAME/KEY: Variant
<222> LOCATION: (7)..(7)
<223> OTHER INFORMATION: Xaa is Gly, Thr, Ala or Glu
<220> FEATURE:
<221> NAME/KEY: Variant
<222> LOCATION: (16)..(16)
<223> OTHER INFORMATION: Xaa is Lys and Gln

<400> SEQUENCE: 19

Leu Ile Asn Pro Xaa Asn Xaa Val Thr Arg Tyr Asn Gln Lys Phe Xaa
1               5                   10                  15

Gly

<210> SEQ ID NO 20
<211> LENGTH: 10

```
<212> TYPE: PRT
<213> ORGANISM: Artificial sequence
<220> FEATURE:
<223> OTHER INFORMATION: Synthetic peptide

<400> SEQUENCE: 20

Glu Ala Lys Arg Glu Trp Asp Glu Thr Tyr
1               5                   10

<210> SEQ ID NO 21
<211> LENGTH: 119
<212> TYPE: PRT
<213> ORGANISM: Artificial sequence
<220> FEATURE:
<223> OTHER INFORMATION: Synthetic peptide

<400> SEQUENCE: 21

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Gly Val Thr Arg Tyr Asn Gln Lys Phe
    50                  55                  60

Lys Gly Arg Val Thr Leu Ile Arg Asp Thr Ser Thr Thr Thr Val Tyr
65                  70                  75                  80

Met Glu Leu Thr Ser Leu Thr Ser Glu Asp Thr Ala Val Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser
        115

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Gly Tyr Ser Phe Thr Gly Tyr Thr Met Asn
1               5                   10

<210> SEQ ID NO 23
<211> LENGTH: 17
<212> TYPE: PRT
<213> ORGANISM: Artificial sequence
<220> FEATURE:
<223> OTHER INFORMATION: Synthetic peptide

<400> SEQUENCE: 23

Leu Ile Asn Pro Tyr Asn Gly Val Thr Arg Tyr Asn Gln Lys Phe Lys
1               5                   10                  15

Gly

<210> SEQ ID NO 24
<211> LENGTH: 119
<212> TYPE: PRT
<213> ORGANISM: Artificial sequence
<220> FEATURE:
<223> OTHER INFORMATION: Synthetic peptide
```

<400> SEQUENCE: 24

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asn Gly Val Thr Arg Tyr Asn Gln Lys Phe
    50                  55                  60

Gln Gly Arg Val Thr Ile Thr Arg Asp Thr Ser Thr Thr Thr Val His
65                  70                  75                  80

Met Glu Leu Thr Ser Leu Thr Ser Glu Asp Thr Ala Val Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser
        115

<210> SEQ ID NO 25
<211> LENGTH: 10
<212> TYPE: PRT
<213> ORGANISM: Artificial sequence
<220> FEATURE:
<223> OTHER INFORMATION: Synthetic peptide

<400> SEQUENCE: 25

Gly Tyr Ser Phe Thr Gly His Thr Met Asn
1               5                   10

<210> SEQ ID NO 26
<211> LENGTH: 17
<212> TYPE: PRT
<213> ORGANISM: Artificial sequence
<220> FEATURE:
<223> OTHER INFORMATION: Synthetic peptide

<400> SEQUENCE: 26

Leu Ile Asn Pro Ser Asn Gly Val Thr Arg Tyr Asn Gln Lys Phe Gln
1               5                   10                  15

Gly

<210> SEQ ID NO 27
<211> LENGTH: 119
<212> TYPE: PRT
<213> ORGANISM: Artificial sequence
<220> FEATURE:
<223> OTHER INFORMATION: Synthetic peptide

<400> SEQUENCE: 27

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asn Gly Val Thr Arg Tyr Asn Gln Lys Phe
    50                  55                  60

Gln Gly Arg Val Thr Ile Thr Arg Asp Thr Ser Thr Thr Thr Val His
65                  70                  75                  80

```
Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser
        115

<210> SEQ ID NO 28
<211> LENGTH: 112
<212> TYPE: PRT
<213> ORGANISM: Artificial sequence
<220> FEATURE:
<223> OTHER INFORMATION: Synthetic peptide

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asp Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ser Gln Ser
                85                  90                  95

Thr His Val Pro Pro Thr Phe Gly Gln Gly Thr Lys Val Glu Ile Lys
            100                 105                 110

<210> SEQ ID NO 29
<211> LENGTH: 16
<212> TYPE: PRT
<213> ORGANISM: Artificial sequence
<220> FEATURE:
<223> OTHER INFORMATION: Synthetic peptide

<400> SEQUENCE: 29

Arg Ser Ser Gln Ser Leu Val His Ser Asp Gly Asn Thr Tyr Leu His
1               5                   10                  15

<210> SEQ ID NO 30
<211> LENGTH: 7
<212> TYPE: PRT
<213> ORGANISM: Artificial sequence
<220> FEATURE:
<223> OTHER INFORMATION: Synthetic peptide

<400> SEQUENCE: 30

Lys Val Ser Asn Arg Phe Ser
1               5

<210> SEQ ID NO 31
<211> LENGTH: 9
<212> TYPE: PRT
<213> ORGANISM: Artificial sequence
<220> FEATURE:
<223> OTHER INFORMATION: Synthetic peptide

<400> SEQUENCE: 31

Ser Gln Ser Thr His Val Pro Pro Thr
1               5
```

<210> SEQ ID NO 32
<211> LENGTH: 122
<212> TYPE: PRT
<213> ORGANISM: Artificial sequence
<220> FEATURE:
<223> OTHER INFORMATION: Synthetic peptide

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Met Ala Trp Val Arg Gln Ala Pro Gly Lys Gly Leu Glu Trp Val
        35                  40                  45

Ser Phe Ile Ser Asn Leu Ala Tyr Ser Ile Tyr Tyr Ala Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Asp Tyr Asp Asn Ile Leu Asp Tyr Val Met Asp Tyr Trp
            100                 105                 110

Gly Gln Gly Thr Leu Val Thr Val Ser Ser
        115                 120
```

<210> SEQ ID NO 33
<211> LENGTH: 10
<212> TYPE: PRT
<213> ORGANISM: Artificial sequence
<220> FEATURE:
<223> OTHER INFORMATION: Synthetic peptide

<400> SEQUENCE: 33

```
Gly Phe Thr Phe Ser Asp Tyr Gly Met Ala
1               5                   10
```

<210> SEQ ID NO 34
<211> LENGTH: 17
<212> TYPE: PRT
<213> ORGANISM: Artificial sequence
<220> FEATURE:
<223> OTHER INFORMATION: Synthetic peptide

<400> SEQUENCE: 34

```
Phe Ile Ser Asn Leu Ala Tyr Ser Ile Tyr Tyr Ala Asp Thr Val Thr
1               5                   10                  15

Gly
```

<210> SEQ ID NO 35
<211> LENGTH: 13
<212> TYPE: PRT
<213> ORGANISM: Artificial sequence
<220> FEATURE:
<223> OTHER INFORMATION: Synthetic peptide

<400> SEQUENCE: 35

```
Tyr Asp Tyr Asp Asn Ile Leu Asp Tyr Val Met Asp Tyr
1               5                   10
```

<210> SEQ ID NO 36
<211> LENGTH: 112

```
<212> TYPE: PRT
<213> ORGANISM: Artificial sequence
<220> FEATURE:
<223> OTHER INFORMATION: Synthetic peptide

<400> SEQUENCE: 36

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Phe Gln Gln Arg Pro Gly Gln Ser
        35                  40                  45

Pro Arg Arg Leu Ile Tyr Val Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Phe Thr Phe Gly Gly Thr Lys Val Glu Ile Lys
            100                 105                 110

<210> SEQ ID NO 37
<211> LENGTH: 16
<212> TYPE: PRT
<213> ORGANISM: Artificial sequence
<220> FEATURE:
<223> OTHER INFORMATION: Synthetic peptide

<400> SEQUENCE: 37

Lys Ser Ser Gln Ser Leu Leu Tyr Ser Asn Gly Lys Thr Tyr Leu Asn
1               5                   10                  15

<210> SEQ ID NO 38
<211> LENGTH: 7
<212> TYPE: PRT
<213> ORGANISM: Artificial sequence
<220> FEATURE:
<223> OTHER INFORMATION: Synthetic peptide

<400> SEQUENCE: 38

Val Val Ser Lys Leu Asp Ser
1               5

<210> SEQ ID NO 39
<211> LENGTH: 9
<212> TYPE: PRT
<213> ORGANISM: Artificial sequence
<220> FEATURE:
<223> OTHER INFORMATION: Synthetic peptide

<400> SEQUENCE: 39

Val Gln Gly Thr His Phe Pro Phe Thr
1               5

<210> SEQ ID NO 40
<211> LENGTH: 115
<212> TYPE: PRT
<213> ORGANISM: Artificial sequence
<220> FEATURE:
<223> OTHER INFORMATION: Synthetic peptide

<400> SEQUENCE: 40

Gln Val Gln Leu Val Glu Ser Gly Ala Glu Val Lys Lys Pro Gly Ala
1               5                   10                  15
```

Ser Val Lys Val Ser Cys Lys Ala Ser Gly Tyr Ile Phe Asn Asn Tyr
            20                  25                  30

Trp Ile Asn Trp Val Arg Gln Ala Pro Gly Gln Gly Leu Glu Trp Met
        35                  40                  45

Gly Gln Ile Tyr Pro Asp Gly Asp Thr Asn Tyr Asn Gly Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Ile Val Tyr Trp Gly Gln Gly Thr Leu Val Thr
            100                 105                 110

Val Ser Ser
    115

<210> SEQ ID NO 41
<211> LENGTH: 7
<212> TYPE: PRT
<213> ORGANISM: Artificial sequence
<220> FEATURE:
<223> OTHER INFORMATION: Synthetic peptide

<400> SEQUENCE: 41

Gly Tyr Ile Phe Asn Asn Tyr
1               5

<210> SEQ ID NO 42
<211> LENGTH: 17
<212> TYPE: PRT
<213> ORGANISM: Artificial sequence
<220> FEATURE:
<223> OTHER INFORMATION: Synthetic peptide

<400> SEQUENCE: 42

Gln Ile Tyr Pro Gly Asp Gly Asp Thr Asn Tyr Asn Gly Lys Phe Lys
1               5                   10                  15

Gly

<210> SEQ ID NO 43
<211> LENGTH: 6
<212> TYPE: PRT
<213> ORGANISM: Artificial sequence
<220> FEATURE:
<223> OTHER INFORMATION: Synthetic peptide

<400> SEQUENCE: 43

Glu Gly Tyr Ile Val Tyr
1               5

<210> SEQ ID NO 44
<211> LENGTH: 24
<212> TYPE: DNA
<213> ORGANISM: Artificial sequence
<220> FEATURE:
<223> OTHER INFORMATION: PCR primer

<400> SEQUENCE: 44
actgtggctg caccatctgt cttc                                          24

<210> SEQ ID NO 45
<211> LENGTH: 25
<212> TYPE: DNA

```
<213> ORGANISM: Artificial sequence
<220> FEATURE:
<223> OTHER INFORMATION: PCR primer

<400> SEQUENCE: 45
ctaacactct ccctgttga agctc                                              25

<210> SEQ ID NO 46
<211> LENGTH: 23
<212> TYPE: DNA
<213> ORGANISM: Artificial sequence
<220> FEATURE:
<223> OTHER INFORMATION: PCR primer

<400> SEQUENCE: 46
agggaaccct ggtcaccgtc tcc                                               23

<210> SEQ ID NO 47
<211> LENGTH: 25
<212> TYPE: DNA
<213> ORGANISM: Artificial sequence
<220> FEATURE:
<223> OTHER INFORMATION: PCR primer

<400> SEQUENCE: 47
tcatttaccc ggagacaggg agagg                                             25

<210> SEQ ID NO 48
<211> LENGTH: 24
<212> TYPE: DNA
<213> ORGANISM: Artificial sequence
<220> FEATURE:
<223> OTHER INFORMATION: PCR primer

<400> SEQUENCE: 48
caagtcagag cctcttatat agtg                                              24

<210> SEQ ID NO 49
<211> LENGTH: 23
<212> TYPE: DNA
<213> ORGANISM: Artificial sequence
<220> FEATURE:
<223> OTHER INFORMATION: PCR primer

<400> SEQUENCE: 49
gtaccttgca cgcagtaata aac                                               23

<210> SEQ ID NO 50
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 50

Glu Phe Arg His Asp Ser Gly Tyr Glu Val His His Gln Lys Leu Val
1               5                   10                  15

<210> SEQ ID NO 51
<211> LENGTH: 18
<212> TYPE: PRT
<213> ORGANISM: Artificial sequence
<220> FEATURE:
```

<223> OTHER INFORMATION: Synthetic peptide

<400> SEQUENCE: 51

Asp Ala Glu Phe Arg His Asp Ser Gly Tyr Glu Val His His Gln Lys
1               5                   10                  15

Leu Val

<210> SEQ ID NO 52
<211> LENGTH: 17
<212> TYPE: PRT
<213> ORGANISM: Artificial sequence
<220> FEATURE:
<223> OTHER INFORMATION: Synthetic peptide

<400> SEQUENCE: 52

Ala Glu Phe Arg His Asp Ser Gly Tyr Glu Val His His Gln Lys Leu
1               5                   10                  15

Val

<210> SEQ ID NO 53
<211> LENGTH: 15
<212> TYPE: PRT
<213> ORGANISM: Artificial sequence
<220> FEATURE:
<223> OTHER INFORMATION: Synthetic peptide

<400> SEQUENCE: 53

Phe Arg His Asp Ser Gly Tyr Glu Val His His Gln Lys Leu Val
1               5                   10                  15

<210> SEQ ID NO 54
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 54

Glu Phe Arg His Asp Ser Gly Tyr Glu Val His His Gln Lys Leu
1               5                   10                  15

<210> SEQ ID NO 55
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 55

Glu Phe Arg His Asp Ser Gly Tyr Glu Val His His Gln Lys
1               5                   10

<210> SEQ ID NO 56
<211> LENGTH: 13
<212> TYPE: PRT
<213> ORGANISM: Artificial sequence
<220> FEATURE:
<223> OTHER INFORMATION: Synthetic peptide
<220> FEATURE:

```
<221> NAME/KEY: MOD_RES
<222> LOCATION: (1)..(1)
<223> OTHER INFORMATION: PYRROLIDONE CARBOXYLIC ACID

<400> SEQUENCE: 56

Glu Phe Arg His Asp Ser Gly Tyr Glu Val His His Gln
1               5                   10

<210> SEQ ID NO 57
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 57

Glu Phe Arg His Asp Ser Gly Tyr Glu Val His His
1               5                   10

<210> SEQ ID NO 58
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 58

Glu Phe Arg His Asp Ser Gly Tyr Glu Val His
1               5                   10

<210> SEQ ID NO 59
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 59

Glu Phe Arg His Asp Ser Gly Tyr Glu Val
1               5                   10

<210> SEQ ID NO 60
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 60

Glu Phe Arg His Asp Ser Gly Tyr Glu
1               5

<210> SEQ ID NO 61
```

```
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 61

Glu Phe Arg His Asp Ser Gly Tyr
1               5

<210> SEQ ID NO 62
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 62

Glu Phe Arg His Asp Ser Gly
1               5

<210> SEQ ID NO 63
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 63

Glu Phe Arg His Asp Ser
1               5

<210> SEQ ID NO 64
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 64

Glu Phe Arg His
1

<210> SEQ ID NO 65
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 65
```

Glu Phe Arg
1

<210> SEQ ID NO 66
<211> LENGTH: 119
<212> TYPE: PRT
<213> ORGANISM: Artificial sequence
<220> FEATURE:
<223> OTHER INFORMATION: Synthetic peptide

<400> SEQUENCE: 66

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asn Thr Val Thr Arg Tyr Asn Gln Lys Phe
    50                  55                  60

Gln Gly Arg Val Thr Ile Thr Arg Asp Thr Ser Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Tyr Trp Gly Gln Gly
            100                 105                 110

Thr Leu Val Thr Val Ser Ser
        115

<210> SEQ ID NO 67
<211> LENGTH: 17
<212> TYPE: PRT
<213> ORGANISM: Artificial sequence
<220> FEATURE:
<223> OTHER INFORMATION: Synthetic peptide

<400> SEQUENCE: 67

Leu Ile Asn Pro Ser Asn Thr Val Thr Arg Tyr Asn Gln Lys Phe Gln
1               5                   10                  15

Gly

<210> SEQ ID NO 68
<211> LENGTH: 119
<212> TYPE: PRT
<213> ORGANISM: Artificial sequence
<220> FEATURE:
<223> OTHER INFORMATION: Synthetic peptide

<400> SEQUENCE: 68

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asn Ala Val Thr Arg Tyr Asn Gln Lys Phe
    50                  55                  60

Gln Gly Arg Val Thr Ile Thr Arg Asp Thr Ser Thr Thr Val His
65                  70                  75                  80

Met Glu Leu Thr Ser Leu Thr Ser Glu Asp Thr Ala Thr Tyr Tyr Cys

```
                    85                  90                  95

Thr Arg Glu Ala Lys Arg Glu Trp Asp Glu Thr Tyr Trp Gly Gln Gly
                100                 105                 110

Thr Leu Val Thr Val Ser Ser
        115

<210> SEQ ID NO 69
<211> LENGTH: 17
<212> TYPE: PRT
<213> ORGANISM: Artificial sequence
<220> FEATURE:
<223> OTHER INFORMATION: Synthetic peptide

<400> SEQUENCE: 69

Leu Ile Asn Pro Ser Asn Ala Val Thr Arg Tyr Asn Gln Lys Phe Gln
1               5                   10                  15

Gly

<210> SEQ ID NO 70
<211> LENGTH: 119
<212> TYPE: PRT
<213> ORGANISM: Artificial sequence
<220> FEATURE:
<223> OTHER INFORMATION: Synthetic peptide

<400> SEQUENCE: 70

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
                20                  25                  30

Thr Met Asn Trp Val Arg Gln Ala Pro Gly Gln Gly Leu Glu Trp Met
            35                  40                  45

Gly Leu Ile Asn Pro Ser Asn Glu Val Thr Arg Tyr Asn Gln Lys Phe
        50                  55                  60

Gln Gly Arg Val Thr Ile Thr Arg Asp Thr Ser Thr Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Thr Tyr Trp Gly Gln Gly
                100                 105                 110

Thr Leu Val Thr Val Ser Ser
        115

<210> SEQ ID NO 71
<211> LENGTH: 17
<212> TYPE: PRT
<213> ORGANISM: Artificial sequence
<220> FEATURE:
<223> OTHER INFORMATION: Synthetic peptide

<400> SEQUENCE: 71

Leu Ile Asn Pro Ser Asn Glu Val Thr Arg Tyr Asn Gln Lys Phe Gln
1               5                   10                  15

Gly

<210> SEQ ID NO 72
<211> LENGTH: 5
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: PYRROLIDONE CARBOXYLIC ACID

<400> SEQUENCE: 72

Glu Phe Arg His Asp
1               5

<210> SEQ ID NO 73
<211> LENGTH: 449
<212> TYPE: PRT
<213> ORGANISM: Homo sapiens

<400> SEQUENCE: 73

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
                20                  25                  30

Thr Met Asn Trp Val Arg Gln Ala Pro Gly Gln Gly Leu Glu Trp Met
            35                  40                  45

Gly Leu Ile Asn Pro Ser Asn Glu Val Thr Arg Tyr Asn Gln Lys Phe
        50                  55                  60

Gln Gly Arg Val Thr Ile Thr Arg Asp Thr Ser Thr Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
              325                 330                 335
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 74
<211> LENGTH: 449
<212> TYPE: PRT
<213> ORGANISM: Artificial sequence
<220> FEATURE:
<223> OTHER INFORMATION: Synthetic polypeptide

<400> SEQUENCE: 74

Gln Val Gln Leu Val Gln Ser Gly Ala Glu Val Lys Lys Ser Gly Ala
1               5                   10                  15

Ser Val Lys Val Ser Cys Lys Ala Ser Gly Tyr Ser Phe Thr Gly His
            20                  25                  30

Thr Met Asn Trp Val Arg Gln Ala Pro Gly Gln Gly Leu Glu Trp Met
        35                  40                  45

Gly Leu Ile Asn Pro Ser Asn Glu Val Thr Arg Tyr Asn Gln Lys Phe
    50                  55                  60

Gln Gly Arg Val Thr Ile Thr Arg Asp Thr Ser Thr Thr Thr Val His
65                  70                  75                  80

Met Glu Leu Thr Ser Leu Thr Ser Glu Asp Thr Ala Thr Tyr Tyr Cys
                85                  90                  95

Thr Arg Glu Ala Lys Arg Glu Trp Asp Glu Thr Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

-continued

```
Ser Val Phe Leu Phe Pro Pro Lys Pro Lys Asp Thr Leu Met Ile Ser
            245             250             255

Arg Thr Pro Glu Val Thr Cys Val Val Val Asp Val Ser His Glu Asp
            260             265             270

Pro Glu Val Lys Phe Asn Trp Tyr Val Asp Gly Val Glu Val His Asn
            275             280             285

Ala Lys Thr Lys Pro Arg Glu Glu Gln Tyr Asn Ser Thr Tyr Arg Val
    290             295             300

Val Ser Val Leu Thr Val Leu His Gln Asp Trp Leu Asn Gly Lys Glu
305             310             315             320

Tyr Lys Cys Ala Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
            340             345             350

Leu Pro Pro Ser Arg Asp Glu Leu Thr Lys Asn Gln Val Ser Leu Thr
            355             360             365

Cys Leu Val Lys Gly Phe Tyr Pro Ser Asp Ile Ala Val Glu Trp Glu
    370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
            420             425             430

Ala Leu His Asn His Tyr Thr Gln Lys Ser Leu Ser Leu Ser Pro Gly
            435             440             445

Lys
```